(12) United States Patent
Gratton et al.

(10) Patent No.: US 7,528,384 B2
(45) Date of Patent: May 5, 2009

(54) METHODS AND DEVICES FOR CHARACTERIZING PARTICLES IN CLEAR AND TURBID MEDIA

(75) Inventors: Enrico Gratton, Urbana, IL (US); Guido Motolese, Carroccio (IT); Abdel Tahari, Savoy, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 353 days.

(21) Appl. No.: 11/342,273

(22) Filed: Jan. 27, 2006

(65) Prior Publication Data

US 2006/0256338 A1    Nov. 16, 2006

Related U.S. Application Data

(60) Provisional application No. 60/648,513, filed on Jan. 31, 2005.

(51) Int. Cl.
*G01N 21/64* (2006.01)
(52) U.S. Cl. .................................. 250/461.2
(58) Field of Classification Search ............. 250/458.1, 250/459.1, 461.1, 461.2, 484.5
See application file for complete search history.

(56) References Cited

U.S. PATENT DOCUMENTS

| | | | |
|---|---|---|---|
| 4,940,332 | A | 7/1990 | Miwa et al. |
| 6,759,662 | B1 | 7/2004 | Li |
| 6,794,659 | B2 | 9/2004 | Barbieri et al. |
| 2003/0092058 | A1 | 5/2003 | Spaulding |
| 2005/0264817 | A1 | 12/2005 | Havard et al. |
| 2006/0114553 | A1* | 6/2006 | Laudo ........................ 359/368 |
| 2006/0129327 | A1* | 6/2006 | Kim et al. ..................... 702/19 |

OTHER PUBLICATIONS

Search report corresponding to international application No. PCT/US06/04696, mailed Dec. 4, 2006.

Tahari et al. (Feb. 2004) "Fluorescence Correlation Spectroscopy in Turbid Media," Presented at the Biophysical Society Meeting, Feb. 18, 2004, Baltimore, Maryland.

Berland et al. (Feb. 1995) "Two Photon Fluorescence Correlation Spectroscopy: Method and Application to the Intracellular Environment," *Biophys. J.* 68:694-701.

Chen et al. (Jul. 1999) "The Photon Counting Histogram in Fluorescence Fluctuation Spectroscopy," *Biophys. J.* 77(1):553-567.

Deller et al. (1999) "Topics in Statistical Pattern Recognition," In; *Discrete-Time Processing of Speech Signals*, IEEE Press, pp. 55-73.

Duda et al. (2001) "Pattern Recognition Systems." In; *Pattern Classification*, Wiley-Interscience, pp. 9-13.

(Continued)

*Primary Examiner*—David P Porta
*Assistant Examiner*—Marcus H Taningco
(74) *Attorney, Agent, or Firm*—Greenlee, Winner and Sullivan, P.C.

(57) ABSTRACT

The invention provides methods and devices for detecting, identifying, classifying and characterizing particles in a fluid sample. Optical analyzers are provided having a rotating and/or translating sample container for measuring the concentrations of fluorescent particles present in very low concentrations and for characterizing fluorescent particles on the basis of size, shape, diffusion constant and/or composition. Scanning optical analyzers are provided using pattern recognitions data analysis techniques and multichannel detection.

5 Claims, 13 Drawing Sheets

OTHER PUBLICATIONS

Elson et al. (1974) "Fluorescence Correlation Spectroscopy. I. Conceptual Basis and Theory," *Biopolymers* 13:1-27.

Kask et al. (Nov. 23, 1999) "Fluorescence-Intensity Distribution Analysis and Its Application in Bimolecular Detection Technology," *Proc. Natl. Acad. Sci. USA* 96:13756-13761.

Magde et al. (1974) "Fluorescence Correlation Spectroscopy. II. An Experimental Realization," *Biopolymers* 13:29-61.

Qing et al. (Jun. 1, 2003) "Convective-diffusion-based fluorescence correlation spectroscopy for detection of a trace amount of *E. coli* in water," App. Optics 42:2987-2994.

Tahari et al. (Feb. 2005) "Fluorescence Correlation Spectroscopy in Turbid Media", Presented at the Biophysical Society Meeting, Feb. 16, 2005, in Long Beach, California.

Tahari et al. (Feb. 2001) "Fluctuation Correlation Spectroscopy in Turbid Media: Detection of Somatic Cells and Bacteria in Body Fluids", Presented at the Biophysical Society Meeting, Feb. 2001, Boston, Massachusetts.

Tahari et al. (Feb. 2002) "The Photon Counting Histogram in Turbid Media", Presented at the Biophysical Society Meeting, Feb. 2002, San Francisco, California.

Tahari et al. (Feb. 2004) "Fluorescence Correlation Spectroscopy in Turbid Media", Presented at the Biophysical Society Meeting, Feb. 18, 2006, Baltimore, Maryland.

Tahari et al. (2002) "The Photon Counting Histogram in Turbid Media: Detection of Somatic Cells and Bacteria in Body Fluids," *Biophys. J.* (*Annual Meeting Abstract*) 82(1):431.

Tahari et al. (2001) "Fluctuation Correlation Spectroscopy (FCS) in Turbid Media: Detection of Somatic Cells and Bacteria in Body Fluids, " *Biophys. J.* (*Annual Meeting Abstract*) 80(1):164.

Tahari et al. (2004) "Fluorescence Correlation Spectroscopy in Turbid Media: Ultrasensitive Detection of Bacteria, Viruses and Protein Aggregates" Website posting Aug. 2004.

Webb, W.W. (Aug. 20, 2001) "Fluorescence Correlation Spectroscopy: Inception, Biophysical Experimentations and Prospectus," *Appl. Opt.* 40:3969-3983.

* cited by examiner

METHODS AND DEVICES FOR CHARACTERIZING PARTICLES IN CLEAR AND TURBID MEDIA

CROSS-REFERENCE TO RELATED APPLICATIONS

This application claims priority under 35 U.S.C. 119(e) to U.S. provisional Patent Application 60/648,513 filed Jan. 31, 2005, which is hereby incorporated by reference in its entirety to the extent not inconsistent with the disclosure herein.

STATEMENT REGARDING FEDERALLY SPONSERED RESEARCH OR DEVELOPMENT

This invention was made with Government support under Contract Number PHS5P41-RR03155 awarded by the National Institutes of Health (NIH). The Government has certain rights in the invention

BACKGROUND OF THE INVENTION

Over the last several decades, optical analysis methods have emerged as useful and broadly applicable analytical tools for detecting and characterizing trace components in wide variety of media. In optical analysis methods, electromagnetic radiation is provided to a sample and interacts with components of the sample. The interaction between incident electromagnetic radiation and the sample generates scattered, transmitted and/or emitted electromagnetic radiation that is collected and detected. The intensities, wavelength distribution, polarization states, scattering angles or any combination of these properties of the detected light provides information relating to the composition, concentration, physical state and/or chemical environment of sample components. Optical analysis methods that have been demonstrated as especially useful for characterizing trace components include absorption and emission spectroscopy techniques, Raman and Mie scattering analysis methods, magnetic resonance spectroscopy methods and multidimensional optical spectroscopy techniques Optical analysis methods provide a number of benefits particularly advantageous for characterizing cellular and noncellular components of biological systems. First, optical analysis methods are applicable to a wide range of biological systems and biological materials, as most biologically significant molecules, such as peptides, oligonucleotides and lipids, and aggregates thereof absorb, scatter and/or affect the polarization states of electromagnetic radiation in ultraviolet, visible and infrared regions. Second, many optical analysis methods provide selective and sensitive means of identifying and characterizing biological materials, particularly methods employing selective optical labeling techniques such as fluorescent labeling or infrared tagging. Third, optical methods often constitute nondestructive characterization methods, thereby allowing components of a biological sample to be analyzed without significantly affecting their biological activities, compositions or physical states. Fourth, optical analysis methods provide in situ, real time detection in static and flowing systems. Finally, recent availability of inexpensive sensitive photodetectors and stable optical sources operating in the ultraviolet, visible and infrared regions of the electromagnetic spectrum makes high throughput analysis using optical methods both commercially and technically practicable.

As a result of these benefits, optical analysis methods are widely used for identifying, classifying and sorting biological materials. Optical flow cytometry, for example, has been demonstrated as useful in a range of diverse experimental settings including immunophenotyping applications, DNA analysis, functional assays, cellular sorting, quantitative analysis of cellular and noncellular particles, and, clinical diagnosis and therapy. In flow cytometry, a suspension comprising cellular and/or noncellular particles of interest are injected into a faster flowing stream of fluid, which provides a sheath around the particles thereby producing laminar flow. The sheath fluid is pumped much faster than the sample in a process known as hydrodynamic focusing, which minimizes clogging and precisely centers sample streams of particles in a small analysis volume. The continuous laminar flow of particles spatially segregates particles such that they pass through an optical detection region where they are characterized. In the optical detection region, particles interact, preferably one at a time, with one or more incident beams of electromagnetic radiation, such as laser light having a selected wavelength distribution, thereby generating scattered, transmitted and/or emitted electromagnetic radiation that is detected as a function of time. Optical measurements typically used in conventional optical flow cytometry systems for characterizing cellular material include low angle forward scattered light intensities for characterizing cell diameter and orthogonal scattered light intensities for determining the quantity of granular structures in a cell.

Fluorescent detection methods are widely employed in convention optical flow cytometry systems, particularly in combination with selective fluorescent labeling techniques, wherein fluorescence intensities corresponding to a plurality of wavelength distributions are simultaneously detected for each particle passing through the optical detection region. Labeled probes and a plethora of fluorescent dyes, stains and intercalators aid in the detection of a wide variety of cell types and cell components. In some methods, fluorescent antibodies are used to measure the densities of specific surface receptors of cellular analytes, and thus to distinguish subpopulations of differentiated cell types. Intracellular components are also routinely detected and quantified using fluorescent probes in combination with optical flow cytometry, including total intracellular DNA, specific nucleotide sequences in DNA or mRNA, selected peptides and proteins and free fatty acids.

Optical flow cytometry techniques, therefore, allow individual cells to be distinguished on the basis of a large number of parameters, such as their location in the fluid stream, size, quantity of granular structures, and the presence and abundance of detectable markers. As result of this capability, optical flow cytometers are often used to generate a diagnostic profile of a population of particles in a biological sample. For example, flow cytometry has been effectively used to measure the decline or maintenance of immune cells during the course of treatment for HIV infection and to determine the presence or absence of tumor cells for prognosis and diagnosis of cancer patients.

Although optical flow cytomtery is a powerful and versatile technique for identifying and characterizing components of biological samples, it has a number of significant limitations and drawbacks. First, the dynamic range of conventional optical flow cytometers with respect to the size of particles analyzed is narrow. As a result of this limitation, a number of different flow cytometers is often required for studying biological systems comprising a distribution of cells having different sizes. Second, proper operation of a flow cytometer requires that there are no clumps of cells or other debris present in the sample subjected to analysis, as these can block or deleteriously impact the laminar flow conditions the flow cell. Samples and sheath fluids, therefore, need to be carefully filtered to prevent obstruction of the flow. The necessary filtration is often troublesome to effectively carry out without affecting flow conditions in a deleterious manner. Third, conventional flow cytometers comprise complex instrumentation that requires highly trained operators for proper operation. Alignment and calibration of flow cytometers are not simple tasks, and need to be performed often to achieve accurate and well resolved optical classification. Fourth, correct operation of a flow cytometer requires the flow cell to be cleaned frequently and the tubing flushed and disinfected to prevent bio-film buildup and contamination. Cleaning and disinfecting is particularly important when using these methods to characterize samples containing microorganisms. Fifth, the sample under investigation is lost after analysis in many flow cytometer systems, and therefore, can not be subjected to additional analysis using complementary techniques. This is a significant disadvantage when analyzing samples available only in minute quantities or hard-to-get samples. Finally, the substantial cost of commercially available flow cytometers, even systems not capable of cell sorting, in addition to significant limitations in their portability, are disadvantages which have prevented widespread use of this technology outside large research and clinical institutions.

It will be appreciated from the foregoing that there is currently a need in the art for optical methods and devices for identifying and characterizing components of sample present in extremely low quantities, particularly trace components of biological samples. Optical analysis methods and devices providing a large dynamic range with respect to the size distribution, composition and physical state of particles analyzed are needed. In addition, optical analysis methods and devices are needed that are less susceptible to bio-film buildup and contamination than conventional optical flow cytometers, and which do not require cumbersome pre-filtration of samples undergoing analysis. Finally, inexpensive, simple and portable optical analysis devices are needed for analyzing biological samples, which can be operated by technicians without extensive training.

SUMMARY OF THE INVENTION

The present invention provides optical methods, devices and device components for analyzing particles in samples, particularly fluorescent particles present in low abundances. The present invention provides scanning confocal microscopy devices and analysis methods for detecting, measuring the concentration of, and classifying particles, including cells, microorganisms, biologically significant molecules and aggregates and complexes thereof, in clear media, scattering media and/or optically opaque media. Methods and devices of the present invention are capable of detecting, identifying and classifying particles having a wide range of sizes using short (e.g. less than about 1 minute) sample scanning periods. It is a goal of the present invention, to provide optical analysis devices and analysis methods capable of detecting particles present in samples in extremely low concentrations, such as attomolar or lower concentrations, and accurately classifying them with respect to physical, chemical and/or optical characteristics. It is another goal of the present invention to provide optical analysis systems and methods that do not require sample filtration and do not result in loss or degradation of a sample during analysis. It is yet another goal of the present invention to provide mechanically simple, mechanically robust, inexpensive, and highly portable optical analysis devices that can be easily operated by technicians without extensive training.

In one aspect, the present invention provides optical analyzers and methods for analyzing particles, such as fluorescent particles, present in a sample. In an embodiment of this aspect of the present invention, the optical analyzer comprises an at least partially transparent container for holding the sample containing particles; an optical source for generating excitation light, a means for collecting fluorescence, a means for moving the container and a photodetector. Use of an optical cuvette, such as a cylindrical cuvette, as an at least partially transparent container for holding the sample containing particles is beneficial for some applications of this aspect of the present invention. In one embodiment, collimated excitation light generated by the optical source, such as a laser or lamp, is provided to the sample. Interaction of the excitation light and the sample causes at least a portion of the particles in the sample to generate fluorescence.

The means for collecting fluorescence, such as a lens, reflector fiber optical element, confocal microscope or waveguide, is positioned in optical communication with the sample and configured such that it selectively collects fluorescence from an observation volume inside the sample and positioned within the container. In embodiments useful for analyzing particles in turbid media, the observation volume is positioned proximate to (e.g. within about 500 microns or in some applications within about 200 microns) of the wall of the at least partially transparent container holding the sample. The means for moving the container is operationally connected to the container such that it is capable of moving the container in a manner that transports at least a portion of the particles in the sample through the observation volume. Exemplary means for moving the container useful in some embodiments are capable of rotating and/or displacing (e.g. vertically displacing, horizontally displacing or both) the container in a manner providing a statistically independent observation volume for a given sample scanning period, and, optionally, provide a means for transporting the particles through the observation volume one particle at a time. The photodetector is provided in optical communication with the means for collecting fluorescence and is capable of receiving fluorescence from the observation volume, measuring intensities of fluorescence from the observation volume and generating a temporal profile of the fluorescence. Optionally, one or more apertures, such as a slit or plurality of slits, is provided between the sample and photodetector to ensure that fluorescence originating from the observation volume is detected by the photodetector and fluorescence from other regions the same is not detected. Optionally, an excitation optical filter is provided between the optical source and the sample and/or an emission optical filter is provided between the sample and the photodetector. In some embodiments, analysis of the temporal profile generated by the photodetector provides a measurement of the concentration, size distribution and/or brightness distribution of particles in the sample.

In an embodiment, the present invention provides an optical analysis device combining a novel scanning confocal microscope and a processor having a pattern recognition algorithm capable of detecting, counting and/or classifying fluorescent particles present at low concentrations in a fluid sample. In one embodiment of this aspect, the present invention provides an optical analysis device for determining the concentration of particles in a fluid sample comprising an at least partially transparent container for holding the fluid sample, an optical source for generating excitation light, a confocal microscope, a means for moving the container holding the sample, a photodetector and a processor having a pattern recognition algorithm. In this embodiment of the present invention, the confocal microscope is provided in optical communication with the optical source such that it receives the excitation light. The confocal microscope focuses the excitation light onto the sample held in the at least partially transparent container, thereby causing particles in the sample to generate fluorescence, and also collects the fluorescence from an observation volume in the sample. The photodetector is provided in optical communication with the confocal microscope, receives at least a portion of the fluorescence from the observation volume and measures its intensity as a function of time, thereby generating a temporal profile of the fluorescence from the observation volume. In one embodiment, a confocal aperture is provided in front of the photodetector having a slit or pin hole area that provides an observation volume having a volume selected from the range of about $1 \times 10^2$ µm$^3$ to about $1 \times 10^8$ µm$^3$. In one embodiment, the confocal aperture is a slit having a width selected from the range of about 1 to about 100 microns.

The means for moving the container is operably connected to the container such that it is capable of moving the container during optical analysis. In one embodiment, the means for moving the container rotates and/or translates the container along a selected trajectory during optical analysis that transports (or sweeps) sample containing particles through the observation volume during a selected sample scanning period, for example by providing rotation and/or displacement of the container in vertical and/or horizontal directions. Optionally, the means for moving the container rotates the container during optical analysis, thereby systematically varying the orientation of particles undergoing analysis with respect to the propagation axis of the excitation light as they are transported through the observation volume. The means for moving the container may provide any motion of the container, cyclical or noncyclical, that effectively transports sample containing particles through the observation volume, rotates the container or provides a combination of both translation and rotational motion. In one embodiment, the means for moving the container is a motor, switching electronics and/or an eccentric rotating plate mechanism capable of rotating, vertically displacing and/or horizontally displacing the container holding the fluid sample. Means for moving the container preferred for some applications provides rotational motion at a selectively adjustable rotational velocity, providing vertical displacement having a selectively adjustable trajectory and rate of displacement and/or providing horizontal displacement having a selectively adjustable trajectory and rate of displacement. In one embodiment, the vertical displacement rate of the container is selected over the range of about 0.01 centimeters per second to about 5 centimeters per second and/or the rotational velocity of the container is selected from the range of about 0.1 revolutions per second to about 10 revolutions per second.

The processor, such as a computer or other hardware equivalent, having a pattern recognition algorithm is provided in at least one way communication with the photodetector for receiving an output signal corresponding to the temporal profile generated by photodetector. Operation of the pattern recognition algorithm analyzes the temporal profile, thereby determining the concentration of particles in the sample. In one embodiment, the pattern recognition algorithm matches features in the temporal profile to predetermined patterns that correspond to the time dependent fluorescence intensities of particles passing through the observation volume. Predetermined patterns useful in the present invention comprise a distribution of intensities as a function of time, and may be determined empirically (for example by measuring the fluorescence temporal profiles corresponding to well characterized sample containing fluorescent particles (e.g. samples containing fluorescently labeled beads)) or calculated ab initio. Pattern recognition algorithms of the present invention may be a component of a larger data filtering algorithm, that identifies features in a temporal profile that correspond to particles passing through the observation volume. In some embodiments, pattern recognition algorithms and data filtering algorithms of the present invention are also able to analyze temporal profiles via fluorescence correlation spectroscopy techniques and photon counting histogram analysis.

Discrete particle detection events are identified by establishing a match between the amplitude and shape of a feature in the temporal profile and a predetermined pattern. The concentration of particles is determined by calculating the number of predetermined patterns matched to features in the temporal profile for a given sample scanning period. In one embodiment, this is performed by operation of a filter algorithm that performs a least squares calculation at each point of a large vector. The algorithm calculates the best amplitude of the filter that minimizes the local chi square, wherein the amplitude is a multiplier of the filter intensity. The chi square is calculated by weighting the difference between the raw data and the fit to the predetermined patterns with the sum of the noise level specified in the noise window and an estimation of the standard deviation that accounts for the square root of the number of counts at the particular point of the large vector. Concentrations are extracted from the analyzed temporal profile by dividing the number of matches by the volume of sample analyzed during a selected sample scanning period, which can be accurately calculated with knowledge of the size of the observation volume, rate of movement of the container (e.g. rate of vertical and horizontal displacement) and the duration of the sample scanning period.

An important functional characteristic of data analysis in the present invention using pattern recognition is that it is capable of accurately correcting for changes in the transmittance, absorbance and/or scattering of fluorescence and excitation light by a moving (e.g. rotating, translating or displaced) cuvette holding the sample undergoing analysis. In some embodiments, this correction amounts to correcting for changes in the background fluorescence and/or scattered excitation light from the observation volume as a function of time. Accordingly, pattern recognition analysis in the present invention enhances the accuracy and reproducibility of measurements carried out using a scanning optical instrumentation wherein the sample container is moved during illumination and optical analysis.

Optionally, operation of the pattern recognition algorithm classifies the particles in the sample on the basis of one or more physical characteristics such as size, shape and diffusion rate, optical properties such as brightness, and/or chemical properties such as the presence and/or abundance of fluorescent and/or fluorescently labeled biomolecules of interest (e.g. peptides, proteins, lipids, m-RNA, oligonucleotides or aggregates and complexes thereof). Characteristics of the ensemble of particles, such as the particle size distribution and the particle brightness distribution, are determined by analysis of the amplitudes and shapes of intensity distributions of the predetermined patterns matched to features in the temporal profile. The width of the predetermined patterns matched to features in the temporal profile, for example the full width at half maximum, can be positively correlated to the residence time of particles in the observation volume. Alternatively, the size of particles passing through the observation volume may be determined by varying the width of a preselected pattern to quantitative match features in the temporal profile. In another embodiment, the integrated brightness of features of the temporal profile and/or predetermined patterns matched to features in the temporal profile provides measurements of physical, optical and/or chemical characteristics of the particles, such as the size and shape of particles in the observation region.

Use of a pattern recognition algorithm for the analysis of fluorescence data is beneficial because it enhances the sensitivity and expands the functional capability of the present optical analysis methods and devices. First, use of a pattern recognition algorithm allows detection of particles having low brightness at concentrations as low as 10 particles per milliliter using sample scanning periods less than one minute. This provides an improvement in sensitivity of about a factor of $10^8$ compared to conventional scanning confocal microscopy methods. Second, pattern recognition algorithms of the present invention allow particles to be classified on the basis of size with any accuracy of about 10%. Moreover, use of a processor having a pattern recognition algorithm provides size analysis methods capable of classifying particles on the basis of size over a wide dynamic range of sizes, such as a range from about 250 nanometers to tens of microns. Finally, pattern recognition algorithms also provide accurate particle classification on the basis of other important particle attributes such as diffusion constant, shape, brightness and composition.

Another advantage of this data analysis approach is that the predetermined patterns useful for analysis via pattern recognition and their use in such analysis algorithms do not strongly depend on particle composition or the composition of the medium that the particles are dispersed in. In the present invention, concentration measurements involve identifying the number of particle detection events and a determination of the net volume of sample scanned during a sample scanning period. Particle detection events are identified by matching a predetermined pattern to a feature in the observed temporal profile of fluorescence from an observation volume. Predetermined patterns of the present invention are capable of being scaled, normalized and/or corrected to account for differences in the diffusion and transport rates of particles in the sample empirically or theoretically with knowledge of the type of particles present in a sample and physical properties, such as density and ionic strength, of the medium containing the particles. Therefore, the present techniques allow determination of the concentration of particles without elaborate calibration procedures strongly dependent on the precise nature of the system undergoing analysis. In the context of particle classification, the present methods and devices employ a calibration procedure which relates the amplitude and shape of predetermined patterns matched to the features in the temporal profile. For example, the size of the particle can be deduced by the time it takes to pass through the confocal volume. In principle, given the size of the slit, the optical magnification and the rotational velocity, the size can be obtained without a priori calibration. However, calibration with particles of known size can also be used in the present invention.

The combination of a confocal microscope and a means for moving the at least partially transparent container holding the sample provides an effective means for transporting substantial volumes (e.g. milliliters) of the fluid sample through the observation volume without requiring use of a flowing system. In the context of this description the term scanning refers to conducting or transporting sample containing particles through an observation volume of a confocal microscope such that particles may be optically detected and/or characterized. In addition, scanning in the present description may also refer to movement of the transparent container such that the position of a particle in the observation volume is changed with respect to the optical axis of the excitation light, for example by rotation of the sample container. In one embodiment of the present invention, the container is simultaneously rotated and vertically displaced to provide scanning of the sample undergoing analysis. Vertical displacement of the container generates a trajectory of the container that passes particles through the observation volume and ensures that the scanned sample volume analyzed during sample scanning is statistically independent. In the context of this description, "statistical independence" with respect to observation volumes analyzed by the present devices and methods refers to the fact that the probability of seeing the same particles in the same configuration during subsequent sweeps is exceedingly small (e.g. less than 0.01%) and in some cases is negligible (e.g. less than 0.0001%). In addition to transporting particles through the observation volume, rotation of the container also systematically varies the position of particles with respect to the optical axis of the excitation light, thereby providing a means of scanning the position of the particles during optical detection. Rotation of the container during optical analysis, therefore, provides a means of characterizing particles as a function of rotational position in the observation region with respect to the propagation axis of the excitation light. Particularly, rotation of the container allows particles to be characterized from a plurality of optical perspectives (i.e. axes passing through the particle) which provides additional information relating to the size, shape and composition of the particles. The combination of rotation (about 5 to about 10 revolutions per second) and slower vertical inversion (about 2.5 to about 5 centimeter per second) of a cylindrical cuvette provides a container trajectory useful for measuring the concentration of particles in a sample at sub-attomolar concentrations and classifying them with respect to size.

The net volume of fluid sample transported through the observation volume during optical analysis (e.g. by rotation, vertical displacement and/or horizontal displacement) depends on the length of scanning period, and the rate of motion of the container holding the sample and the size of the observation volume. The size of the observation volume is controlled by the size of the confocal aperture employed in the confocal microscope, particularly the size of a confocal aperture positioned between the sample and the photodetector. Smaller observation volumes are beneficial for increasing the signal to background ratio and ensuring particles pass through the observation volume and are detected one at time. Use of smaller observation volumes, however, requires longer sample scanning periods to analyze equivalent net sample volumes as analyzed in systems using larger observation volumes. Accordingly, selection of the observation volume and sample scanning time represents a trade off in these device performance attributes. In some applications, the best compromise is to use the largest confocal aperture that provides accurate detection and characterization of the particles of interest. By increasing the observation volume (using a wider confocal aperture), the total volume scanned for a given run time is larger. Alternatively, samples undergoing optical analysis may be diluted prior to analysis to achieve a concentration that ensures that particles are transported through a detection volume one at a time. Sample dilution may also be useful when characterizing particles dispersed in highly scattering or absorbing media.

This combination of device components for scanning a sample during optical analysis provides number of tangible benefits in the methods and devices of this aspect of the present invention. First, use of a confocal microscope in combination with a means for moving the sample container provides a means for transporting particles through an observation region while avoiding the need for generating a fluid flow. As a result, the sample undergoing analysis does not require extensive prefiltration to prevent problems associated with sample flow and clogging, as in optical flow cytometry systems. In addition, sample never enters the inner workings of the device, thereby making the present analysis systems less susceptible to problems associated with contamination, bacterial growth and formation of bio-films. Furthermore, the sample is not lost, damaged or degraded during optical analysis, thereby allowing the sample to be subjected to additional and complementary analyses after detection and characterization by the present methods. Second, use of a confocal microscope enables use of very small observation volumes, as small as picoliters, which are useful for ensuring that particles pass through the observation region one at a time and improving signal to noise ratio. Vertical displacement and rotation of the container, however, allows for large volumes of sample, such as sample volumes equal to about 1 millimeter to about 10 milliliters, to be characterized using relatively short sample scanning periods, such as scanning periods equal to about 1 second to about 100 seconds. Third, use of a confocal microscope allows an illumination focus to be selected such that the observation region is positioned relatively close (e.g. about 50 microns to about 500 microns) to the walls of the container holding the sample. This feature allows the components of partially transparent and/or highly scattering media, for example turbid media, to be effectively analyzed using the present devices and methods. Fourth, use of a confocal microscope in combination with a means for moving the sample container provides a means for transporting sample containing particles through an observation region without requiring complex optical systems comprising moveable optical components, such as translating optical sources, photodetector or dichroic mirrors. This aspect of the present invention is advantageous as it provides a simple, mechanically robust experimental system that does not require repeated optical realignment between scans.

In another aspect, the present invention provides method and devices for selectively detecting and measuring the concentration of particles in a fluid sample, and optical analysis methods and devices capable of discriminating between particles having different physical properties and/or chemical properties. In some embodiments of this aspect of the present invention, detection specificity is provided by treating the sample with one or more fluorescent probes, such as fluorescent dyes, stains, covalent tags and/or intercalators, that selectively associate (covalently or noncovalently) with specific components of a sample, such as surface bound, intercellular or intracellular proteins, peptides, lipids, oligonucelotides or any aggregates or complexes thereof. For example, the present methods and devices are well suited for analysis of fluid samples that have been treated with a plurality of different fluorescent probes, such as nucleic acid fluorophors and fluorescent antibodies, that selectively associate with different components of a sample. In this embodiment, simultaneous or sequentially excitation with light of different wavelength distributions, and detection of fluorescence at a plurality of different wavelengths allows for discriminate detection and quantification of particles in a sample that selectively associate with one or more fluorescent probes. Alternatively, detection specificity is provided in some methods and devices of the present invention on the base of the diffusion constants of particles passing through the observation volume. In these embodiments of the present invention, the intensity distributions of features in a temporal profile of fluorescence from the observation are analyzed to determine the diffusion constant associated with a detected particle. For example, in some instances the width of a feature in the temporal profile or predetermined pattern matched to a feature in the temporal profile is positively correlated to the diffusion constant or residence time of the particles in the observation volume. As different types of particles, such as particles of different size, shape or electric charge, have different diffusion constants, this functional capability of the present invention provides a means for discriminating between different particle types in a sample. Alternatively, detection specificity is provided in some methods and devices of the present invention on the base of measured particle brightness. In these embodiments, the total integrated intensities of features in the temporal profile are determined and used to differentiate different types of particles. In some instances, for example, this aspect of the present invention provides a means of distinguishing particles, such as cells or microorganisms, on the basis of the presence and abundance of specific biological molecules, such as proteins, peptides, lipids and oligonucelotides, which selectively bind to one or more fluorescent probes administered to the sample.

In another aspect, the present invention provides multichannel optical analyzers capable of simultaneously and independently monitoring fluorescence from a plurality of different fluorescent probes associated with particles transported through an observation region. In one embodiment, a plurality of photodetectors, wavelength discrimination elements and corresponding confocal apertures are provide in optical communication with a confocal microscope, and a plurality of fluorescent probes having different excitation and/or emission wavelengths are provided to the fluid sample undergoing analysis. The composition of each fluorescent probe is selected such that it associates selectively with materials of interest in the sample, for example by using a plurality of different nucleic acid fluorophores or fluorescent antibodies that selectively bind to different surface bound or intracellular proteins or peptides. Excitation by light from one or more optical sources causes particles labeled with one or more probes to fluoresce. The intensities and wavelength distribution of the fluorescence depends on the abundances and identities of fluorescent probes associated with the particles, and thus, can be used to classify the particles on the basis of composition. A plurality of photodetectors is provided with wavelength discrimination elements, such as optical filters, gratings, prisms, monochromators or dichroic reflectors, such that each are capable of detecting the fluorescence originating from a selected fluorescent probe and do not detect fluorescence originating from other fluorescent probes associated with the particle. Accordingly, each photodetector in this optical arrangement independently generates a temporal profile of fluorescence from the observation volume corresponding to a selected fluorescent probe. This embodiment of the present invention is beneficial because it provides good detection specificity, as the particles of interest may be tagged with more than one fluorescent probe emitting in different regions of the electromagnetic spectrum. Analysis of the output of two or more photodetectors for coincident detection events allows for discriminate detection and quantification of the particles of interest.

In another aspect, the present invention provides multichannel optical analyzers wherein a plurality of photodetectors is provided each having a differently sized confocal aperture (e.g. slit) in optical communication with the confocal microscope. In this embodiment, the photodetectors detect light from observation volumes having different effective focal volumes. Observation volumes simultaneously analyzed in the present invention may be positioned so as to overlap, and in some embodiments are concentrically disposed. Simultaneous analysis of fluorescence temporal profiles for observation volumes corresponding to different effective focal volumes aids in more accurately resolving the size distribution of particles in the sample because the size of the particle will change the transit time through the confocal slit. Different confocal apertures can be used to determine the size and/or brightness of the particle more accurately. Furthermore, the position of the particle along the direction of the optical axis can be determined using multichannel systems of this embodiment.

The present invention also includes methods and devices employing statistical analysis methods in addition to, or other than, pattern recognition analysis techniques. In one embodiment, for example, the present invention provides devices and methods wherein an observed temporal profile is analyzed via operation of a photon histogram analysis algorithm that generates a histogram of detected photons. Photon counting histograms acquired using this analysis method characterize the amplitude distribution of fluctuations of fluorescent light emanating from the observation volume, and relate to the probability distribution to detect a given number of photons per sampling time. For a single species of fluorescent particles, a photon counting histogram may be characterized by two parameters: the average number of particles in the observation volume, and the particle brightness, which is defined as the average number of detected photons per sampling time per particle. In addition, it is possible to use photon counting histogram analysis to distinguish different fluorescing species present in a sample if they have sufficiently spaced brightness magnitudes. Alternatively, the present invention provides devices and methods wherein an observed temporal profile is analyzed via operation of a fluorescence correlation analysis algorithm. An exemplary fluorescence correlation analysis algorithm of the present invention determines the temporal autocorrelation of the fluorescence fluctuations, which provides a measurement of the temporal duration of fluorescence fluctuations as a function of time. This analysis provides information related to the number of molecules in the observation volume, and processes and parameters that determine fluctuations in the observed fluorescence, such as the diffusion constants and diffusion rates of detected particles.

In another aspect, optical analysis devices and methods of the present invention are capable of closed loop feedback control on the basis of control signals derived from the fluorescence intensity profiles of particles passing through the observation volume. This aspect of the invention provides optical analysis methods devices wherein selected particles in a fluid sample can be detected and characterized multiple times. In embodiments of this aspect of the present invention, sample containing particles is transported through the observation volume by translation of the container holding the sample along a selected container trajectory. Fluorescence from particles in the observation region is collected thereby generating a temporal profile, which is analyzed in real time by a processor. The processor has a pattern recognition algorithm for analyzing the temporal profile and is provided in at least one way communication with a controller capable of selectively adjusting the trajectory of the moving container. Characteristics of the particle are determined in real time via analysis of the temporal profile and serve the basis of one or more control signals provided to the controller. In one embodiment, control signals provided to the controller which indicate a new container trajectory capable of transporting a selected particle through the observation region a plurality of times during a sample scanning period. For example, the physical or chemical characteristics of a detected particle may indicate that further optical analysis is required to adequately classify the particle, and therefore, the processor generates control signals initiating a modified container trajectory capable of transporting the particle of interest through the observation volume, thereby, providing one or more additional particle detection events.

The present invention also provides integrated particle measurement systems capable of providing integrated measurements of the concentrations of particles introduced to a fluid sample undergoing optical analysis. In this aspect of the present invention, the container holding the sample is operationally connected to a means of introducing particles into the sample. In one embodiment, for example, a tube is provided to the container for bubbling gas through the sample or introducing fluids, continuously or drop wise, prior to and/or during optical analysis. A fluid introduction system may be connected to the container capable of providing drops of liquid containing particles to the sample. In these embodiments, particles are systematically provided to the container, continuously or at discrete times. The optical analysis device of the present invention periodically or continuously probes the sample, thereby providing characterization of particles in a sample as a function of time. In one embodiment, for example, an integrated particle measurement system of the present invention provides measurements of the concentration, size distribution, composition, brightness or any combination of these characteristics of particles that accumulate in the fluid sample. This aspect of the invention is particularly useful for detecting pathogens and/or contaminants in environmental samples, such as room air or in water samples.

The methods and devices of the present invention are broadly applicable to optical analysis of particles undergoing emission via photoluminescence, chemiluminescence and or electroluminescence processes in an observation volume of a confocal microscope. For example, the present devices and methods are useful for identifying, classifying and/or determining the concentration of particles capable of undergoing chemiluminescence and/or bioluminescence. In these aspects of the present invention, emission from particles passing through the observation volume of a confocal microscope is collected, detected and analyzed without the need for providing excitation light to the sample. Fluorescence in the present methods may be excited by single photon absorption processes or multiphoton absorption processes. An advantage provided by use of multiphoton excitation in the present methods, such as two photon excitation schemes, is that fluorescence from very small observation volumes having excitation light intensities large enough to generate appreciable multiphoton absorption can be collected, detected and analyzed.

The present methods and devices are useful for characterizing samples comprising a wide variety of materials including, but not limited to, liquids, colloids, dispersions suspensions, emulsions, sols and mixtures. The present methods and devices are useful for detecting naturally fluorescing and fluorescently labeled components in high transparent media, partially transparent media and in highly scattering media. The present invention provides nondestructive optical analysis methods particularly well suited for the analysis of biological samples, such as bodily fluids, tissue suspensions, food and beverages, fluids generated from expression systems, such as recombinant expression systems, and samples derived from these. The present methods are capable of detecting and classifying biological materials at low concentrations including, but not limited to, prokaryotic cells, eukaryotic cells, bacteria, virus, biological molecules such as proteins, peptides, oligonucelotides, DNA, mRNA, lipids, and all aggregates and complexes thereof. This high degree of versatility with respect to the composition of materials analyzed by the present devices and techniques makes them suitable for a wide range of applications including, but not limited to, characterizing cellular material and microorganisms, identifying biological molecules present in biological samples, assaying materials present in food stuff, detection of pathogens in samples, assaying of biological samples for clinical diagnostic and therapeutic applications, high throughput quantitative analysis of samples, and functional assays for monitoring protein expression rates.

In another embodiment, the present invention provides a method for analyzing particles in a sample comprising the steps of: (i) providing the sample containing particles in an at least partially transparent container; (ii) directing excitation light onto the sample, thereby causing at least a portion of the particles in the sample to generate fluorescence; (iii) collecting fluorescence from an observation volume in the sample and directing the fluorescence from the observation volume onto a photodetector; (iv) moving the container thereby passing particles in the sample through the observation volume; and (v) measuring the intensity of the fluorescence from the observation volume as a function of time using the photodetector, thereby generating a temporal profile of the fluorescence corresponding from the observation volume. Optional methods of this aspect of the present invention may further comprise the step of analyzing the temporal profile using a pattern recognition algorithm.

In another aspect, the present invention provides a method for determining the concentration of particles in a sample containing the particles comprising the steps of: (1) providing the sample containing particles in an at least partially transparent container; (2) directing excitation light onto a confocal microscope in optical communication with the sample containing particles; (3) focusing the excitation light onto the sample using the confocal microscope, thereby causing the particles to generate fluorescence; (4) collecting the fluorescence from an observation volume in the sample using the confocal microscope; (5) translating the container thereby passing particles in the sample through the observation volume; (6) measuring the intensity of the fluorescence from the observation volume as a function of time using a photodetector positioned in optical communication with the confocal microscope, thereby generating a temporal profile of the fluorescence corresponding from the observation volume; and (7) analyzing the temporal profile using a pattern recognition algorithm thereby determining the concentration and size of the particles in the sample from the temporal profile.

BRIEF DESCRIPTION OF THE DRAWINGS

FIGS. 16A and 16B schematic depict embodiments of the present invention using a single-slit confocal aperture and FIGS. 16C and 16D depict embodiments of the present invention using a dual-slit confocal aperture.

DETAILED DESCRIPTION OF THE INVENTION

Figure 1A:
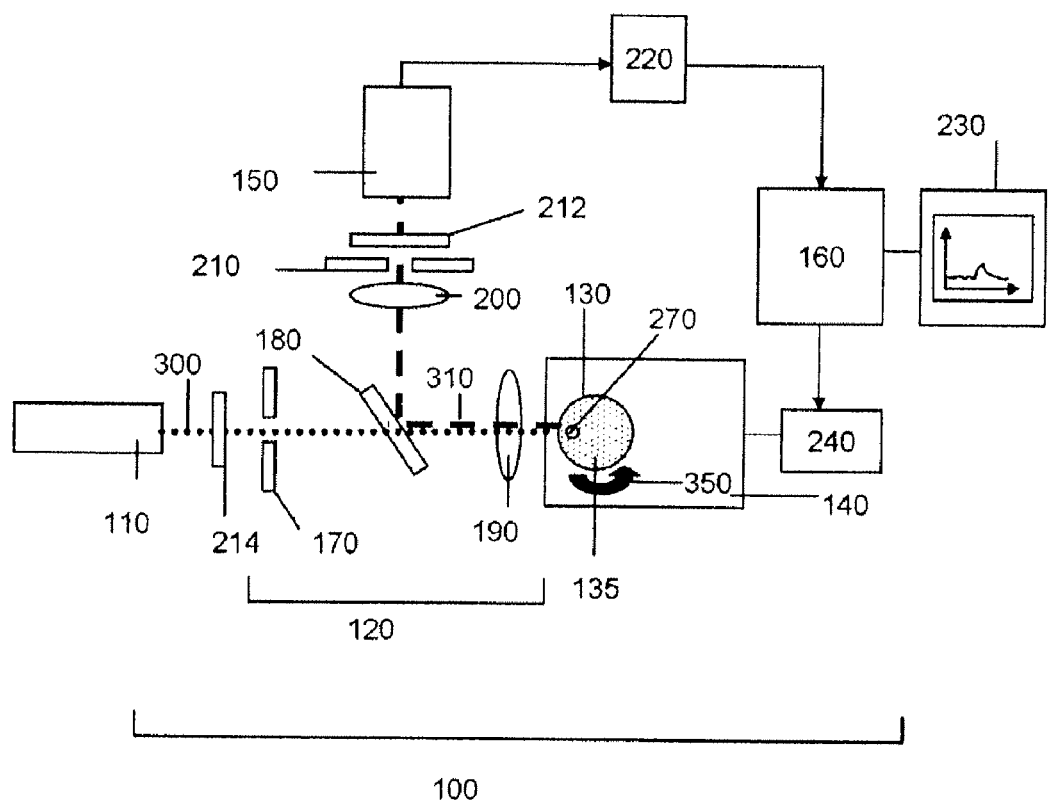
FIG. 1A provides a schematic diagram of a top plan view of an optical analysis device of the present invention for measuring the concentration of fluorescent particles in a fluid sample.

Referring to the drawings, like numerals indicate like elements and the same number appearing in more than one drawing refers to the same element. In addition, hereinafter, the following definitions apply:

"Fluid" and "Fluid sample" are used synonymously and refer to any material which is capable of conforming to the shape of a container in which it is held. Fluids useable with methods of the present invention include, but are not limited to, liquids, and mixtures of more than one liquid, colloids such as foams, emulsions, sols, dispersion of particles, suspensions of particles and any combination of these. Fluids in the present description includes biological fluids such as urine, blood, spinal fluid, cellular and noncellular blood components including plasma, platelet-containing samples, red blood cell-containing samples, white blood cell-containing samples, tissue extracts and tissue suspensions, food stuffs, fermentation media generated from recombination methods, materials produced by recombinant techniques including therapeutic and diagnostic materials, materials produced from transgenic animals and plants including therapeutic and diagnostic materials, milk and milk products, water, beverages, chemical and pharmaceutical products, and vaccines.

"Particles" refer to soluble and insoluble materials present in a sample. Particles in the present description includes, but is not limited to, molecules, ions, polymers, biological molecules, cells such as eukaryotic and prokaryotic cells, components of cells, microorganisms such as bacteria and viruses, pathogens and all, components, complexes and aggregates of these. "Biological molecules" refers to molecules that are produced by an organism or are important to a living organism, including, but not limited to, proteins, peptides, peptide hormones, lipids, DNA molecules, RNA molecules, oligonucleotides, carbohydrates, polysaccharides; glycoproteins, lipoproteins, sugars and derivatives, variants, aggregates and complexes of these, including labeled analogs of these having one or more fluorescence label. "Fluorescent particles" refers to particles capable of generating fluorescence when excited by excitation light, and includes intrinsically fluorescent particles and particles that are fluorescently by virtue of their association (covalent or noncovalent) with one or more flourophors including fluorescently labeled particles, stained particles, fluorescently tagged particles, and particles associated with an intercalator or dye. Fluorescent particles may be associated with a single fluorophor or a plurality of fluorophors. Fluorescent particles may be selectively labeled or tagged with fluorophors that selectively associated with a specific type of particle or specific elements of such particles, such as proteins and/or oligonucleotides.

"Fluorescence temporal profile" refers to the distribution of fluorescence intensity as a function of time. "Features" in a fluorescence temporal profile refers portions of a temporal profile characterized by changes in intensity as function of time, preferably for some applications statistically significant changes in intensity as function of time. Features of a fluorescence temporal profile may result from the presence of and/or passage of one or more particles through the observation volume of the present devices and methods.

"Optical communication" and "optically coupled" are used synonymously in the present description and refer to a configuration of two or more device elements wherein light is capable of propagating from one element to another element. Device elements can be optically coupled directly or indirectly using a variety of device components including, but not limited to, wave guides, fiber optic elements, reflectors, filters, prisms, lenses, gratings and any combination of these device components.

The terms "intensity" and "intensities" refers to the amplitude(s) of electric or magnetic field vector of light, such as excitation light or fluorescence. The terms "intensity" and "intensities" may alternatively refer to the amplitude(s) of the signal generated by a photodetector upon detection of light, for example the amplitude(s) of current generated by a photodiode or photomultiplier tube.

The terms "electromagnetic radiation" and "light" are used synonymously in the present application and refer to waves of electric and magnetic fields. Electromagnetic radiation useful for exciting fluorescent particles in the device and methods of the present invention includes ultraviolet light, visible light, near infrared, far infrared or a combination of these.

"Partially transparent" refers to the property of a material, device or device component capable of transmitting at least a portion of electromagnetic radiation incident upon it.

"Translation" refers to displacement of a device or device component, such as movement of an at least partially transparent container for hold a sample undergoing analysis. Translation may comprise any type of motion including, but not limited to, vertical displacement, horizontal displacement, circular orbital motion, elliptical orbital motion, parabolic motion, linear motion and any combination of these. Translation may provide cyclical motion or noncylical motion.

"Predetermined pattern" refers to the functional form of a distribution of intensities as a function of time that is matched or fit to features in a temporal profile. Predetermined patterns used for matching features may be derived by ab initio methods, such as using an appropriately scaled or normalized Gaussian or Lorentizian function, or may be derived empirically, for example, by measuring intensity distributions corresponding to passage of particles having known size, shape and brightness through the observation volume. Predetermined patterns may be scaled, normalized or adjusted to optimize a match of the predetermined pattern to a feature in a fluorescence temporal profile. The functional form of predetermined patterns useful in the present invention depends on a number of experimental parameters characterizing the optical detection and characterization system including, but not limited to, the alignment of the excitation and detection optics, and the width of the aperture positioned in front of the photodetector. In addition, the functional form of predetermined patterns useful in the present invention may also depend on characteristics of particles undergoing detection and/or characterization, such as the size of a particle relative to the volume of the point spread function of the confocal microscope, the shape of a particle and the brightness of a particle.

In the following description, numerous specific details of the devices, device components and methods of the present invention are set forth in order to provide a thorough explanation of the precise nature of the invention. It will be apparent, however, to those of skill in the art that the invention can be practiced without these specific details.

This invention provides methods and devices for detecting, identifying, classifying and characterizing particles in a fluid sample. Particularly, the present invention provides scanning confocal microscopy devices using pattern recognitions data analysis techniques for measuring the concentrations of fluorescent particles present in very low concentrations and for characterizing fluorescent particles on the basis of size, shape, diffusion constant and/or composition.

FIG. 1A provides a schematic diagram of a top plan view of an optical analysis device of the present invention for measuring the concentration of fluorescent particles in a fluid sample. The optical analysis device 100 comprises an optical source 110, a confocal microscope 120, and an at least partially transparent container 130, such as an optical cuvette, for holding the fluid sample 135 containing particles, a means for moving the container 140, a photodetector 150 and a processor having a pattern recognition algorithm 160. In the embodiment shown in FIG. 1A, confocal microscope 120 comprises a collimation element (e.g. a pinhole or slit) 170, dichroic reflector 180, first objective lens 190, second objective lens 200 and confocal aperture 210 (e.g. pin hole or slit). Optionally, optical analysis device 100 may further comprise emission filter 212, excitation filter 214, analog-to-digital converter 220, display 230 and device controller 240.

Optical source 110 generates excitation light (schematically represented by dotted line 300) which is provided to confocal microscope 120. Excitation light optionally passes through collimation element 170, thereby generating collimated excitation light that is directed onto dichroic mirror 180. At least a portion of the collimated excitation light passes through the first objective lens 190, which focuses the excitation light on to the sample 135. The focused excitation light is at least partially transmitted through the wall of container 130 and is focused into a small observation volume 270 positioned within the sample 135. Excitation light 300 provided to the sample excites fluorescent particles, which generate fluorescence. A portion of the fluorescence from the observation volume 270 (schematically represented by dashed line 310) is collected by the confocal microscope 120 and provided to photodetector 150, which measures the intensity of fluorescence 310 as a function of time. Although fluorescence 310 typically propagates along a propagation axis coincident with the propagation axis of excitation light 300, it is depicted in FIG. 1A (and also in FIG. 5) as slightly displaced from excitation light 300 so as to provide a means of distinguishing excitation light from fluorescence for the sake of describing these Figures. In the embodiment illustrated in FIG. 1A, fluorescence 310 from observation volume 270 is reflected by dichroic reflector 180, passes through second objective lens 200 and confocal aperture 210, and is imaged on the sensing surface (e.g. photocathode or photodiode) of photodetector 150. Use of confocal aperture 210 prevents fluorescence light not originating from the focal plane of the first objective lens from reaching the sensing surface of photodetector 150. The present invention includes embodiments not having a collimation element 170, particularly when optical source 110 comprises a laser providing beam of excitation light that is spatially collimated without the need of further collimation.

During optical analysis, means for moving the container 140 moves container 130 along a selected trajectory, thereby transporting sample containing particles through the observation volume 270. Preferably for some applications, particles are transported in and out of the observation volume one at a time. In the embodiment illustrated in FIG. 1A, means for moving the container 140 simultaneously rotates container 130 about a rotational axis passing through the center of the container and intersecting the propagation axis of excitation light and vertically displaces container 130 along an axis, for example an axis substantially parallel to or coincident with the axis of rotation of container 140. The rotation of container 130 is schematically illustrated by arrow 350 and the vertical displacement of container 130 is schematically illustrated by arrow 360 (See, FIG. 1B).

Figure 1B:
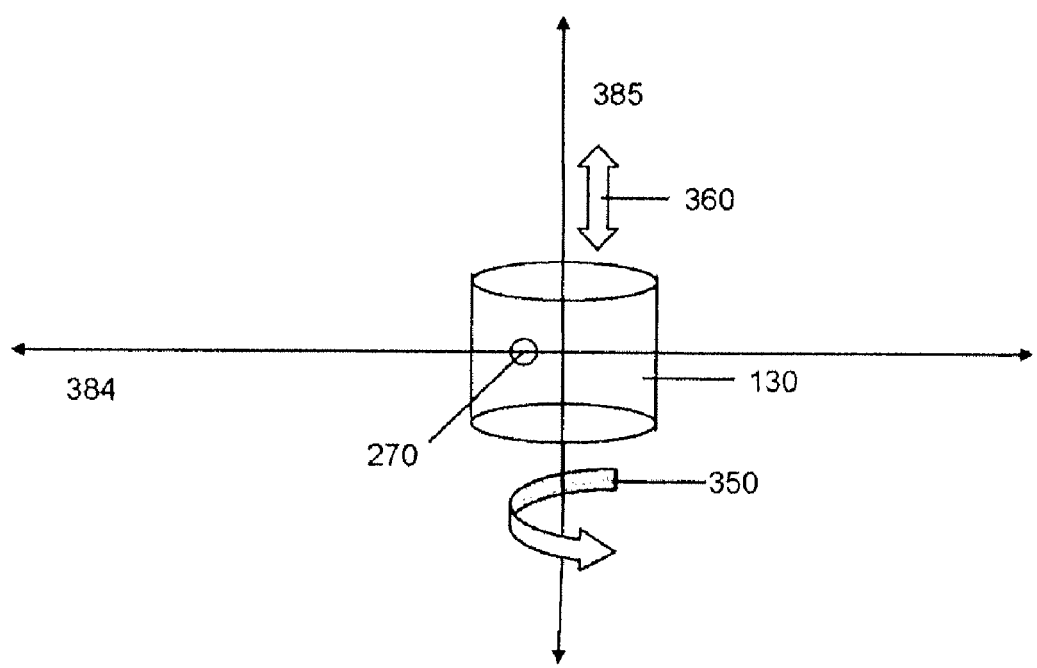
FIG. 1B shows an expanded side view of a container comprising a cylindrical cuvette, and also indicates coincident rotational and vertical displacement axes useful in some methods of the present invention.

FIG. 1B shows an expanded side view of container 130 comprising a cylindrical cuvette. FIG. 1B also indicates observation volume 270 in sample 135. Also shown in FIG. 1B is rotational-vertical displacement axis 385 and propagation axis 384 of the excitation light. As schematically illustrated by arrows 350 and 360 container 130 is simultaneously rotated about rotational-vertical displacement axis 385 and vertically displaced along rotational-vertical displacement axis 385. This combination of rotation and vertical translation of container 130 transports sample containing particles through observation volume 270 and systematically varies the position of particles in the observation volume 270 relative to propagation axis 384 of the excitation light. In embodiments useful for optimizing the signal-to-noise ratios corresponding to measured fluorescence intensities, the rate of rotation and/or vertical displacement is selectively adjustable. The present invention includes embodiments wherein container 130 is moved in a manner other than the combination of rotation and vertical displacement, including translation providing horizontal displacement in combination with rotation, vertical displacement or both rotation and vertical displacement.

Optionally, excitation light 300 is passed through excitation filter 214 positioned in front of optical source 110 that is capable of transmitting wavelengths of light capable of exciting particles in the sample and is capable of substantially preventing transmission of wavelengths of light corresponding to the fluorescence 310 generated upon excitation of fluorescent particles. Optionally, fluorescence 310 is passed through emission filter 212 positioned in front of photodetector 150 that is capable of transmitting wavelengths of light corresponding to the fluorescence 310 and is capable of substantially preventing transmission of wavelengths of light corresponding to the excitation wavelengths of fluorescent particles in the sample. Optionally, dichroic reflector 180 is capable of wavelength discrimination, for example by preferentially transmitting excitation light 300 and preferentially reflecting fluorescence 310. Wavelength discrimination provided by excitation filter 214, emission filter 212, dichroic reflector 180 or any combination of these optical components enhances the overall sensitivity of optical analysis device 100 with respect to detecting, measuring the concentration of and analyzing particles.

The intensity of fluorescence 310 is detected by photodetector 150 as a function of time, thereby generating a temporal profile of fluorescence from observation volume 270. In the embodiment illustrated in FIG. 1, output signals corresponding to the photocurrent of photodetector 150 is transformed from an analog signal to a digital signal by analog-to-digital converter 220, and output signals are directed to processor 160, such as a microcomputer, having a pattern recognition algorithm. The arrows shown in FIG. 1 indicate communication of output signals originating from photodetector 150. Operation of the pattern recognition algorithm, matches predetermined patterns to features in the temporal profile, and counts the number of matches during a given sample scanning time. Predetermined patterns used for matching features may be derived by ab initio methods, such as using an appropriately scaled or normalized Gaussian or Lorentizian function, or may be derived empirically, for example, by measuring intensity distributions corresponding to passage of particles having known size, shape and brightness through the observation volume. As the features matched to predetermined patterns correspond to particles detected in the sample, a measurement of the concentration of particles can be extracted with knowledge of the net volume of sample passed through the observation volume for a given sample scanning period. In one embodiment, the net volume of sample passed through the observation volume for a given sample scanning period is determined by multiplying the net length of the trajectory of the container 130 for a given sample scanning period by the volume of the point spread function of the confocal microscope 120. Use of a confocal microscope having a volume of the point spread function of equal to about $1 \times 10^6$ $\mu m^3$ and sample scanning times on the order of 1 minute allows net volumes to be passed through the observation region on the order of milliliters. In some application use of observation volumes having a volume of the point spread function selected over the range of about $1 \times 10^5$ $\mu m^3$ to about $5 \times 10^7$ $\mu m^3$ is preferred. Pattern recognition algorithms of the present invention may be a component of a data filtering algorithm that identifies and counts features in a temporal profile corresponding to the passage of particles through an observation volume.

Optionally, operation of the pattern recognition algorithm also classifies the particles in the observation on the basis of size and/or shape. In one embodiment, classification is achieved by evaluating the amplitude and shape of predetermined patterns matched to features in the temporal profile. For example, the width of the predetermined pattern matched to features in the temporal profile is correlated to the residence time of a particle in the observation volume, size of a particle, shape of a particle, or the diffusion constant of a particle. Optionally, operation of the pattern recognition algorithm also classifies the particles in the observation volume on the basis of particle brightness by determining the total integrated intensity of predetermined patterns matched to features in the temporal profile. In some instances, discrimination of particles on the basis of brightness provides information related to the identities and abundance of molecules bound to selective fluorescent labels, such as fluorescent antibody tags or fluorescent DNA probes.

Optionally, operation of the pattern recognition algorithm also generates one or more statistical indicators characterizing the quality of the fit of the pre-determined patterns to the observed temporal profile, for example by providing parameters, such as chi-square values, indicating the statistical significance of each matched feature. In one embodiment, the pattern recognition algorithm of the present invention calculates the chi-square for each match by weighting the difference between a feature and the predetermined pattern matched to the feature with an estimation of the standard deviation of each measurement. Optionally, operation of the pattern recognition algorithm also generates an output that presents the processed data and results, such as concentration of particles, size distribution of particles and/or brightness distribution of particles, in a format that is easily evaluated by an operator. In one embodiment, for example, the pattern recognition algorithm generates a histogram showing the number of matched features corresponding to the maximum intensities or total integrated intensities of matched features.

Referring again to FIG. 1A, optical analysis device 100 optionally further comprises device controller 240 and/or display 230. Device controller 240 is operably connected to the means for moving the container 140 and is provided in at least one way communication with processor 160. In one embodiment, device controller receives output signals from processor 160 (schematically shown as an arrow) and is capable of generating a selected trajectory of container 130 having selected rate of displacement, for example a trajectory that repeatedly passes a selected particle of interest through the observation volume 270. Display 230 is provided in at least one way communication with processor 160 and is capable of displaying unprocessed fluorescence data, processed data such as a temporal profile matched to predetermined patterns and other results of the operation of pattern recognition algorithm such as number of features matched to predetermined patterns, concentration of particles, the size distribution of particles, the brightness distribution of particles and statistical indicators characterizing the quality of the fit to the observed temporal profile.

Figure 2:
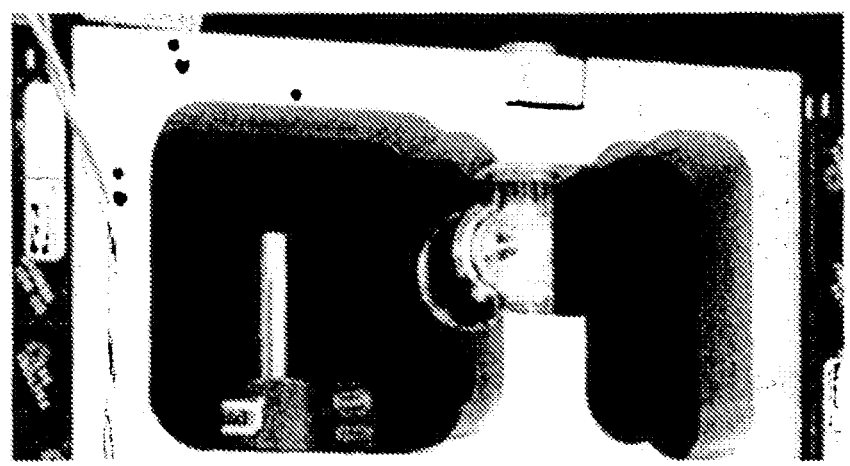
FIG. 2 provides a photograph of an optical analysis device of the present invention comprising a scanning confocal microscope in combination with processor having a pattern recognition algorithm.

FIG. 2 provides a photograph of an optical analysis device of the present invention comprising a scanning confocal microscope in combination with processor having a pattern recognition algorithm. The apparatus shown in FIG. 2 comprises a small confocal microscope that has a horizontal geometry and a mechanical instrument that holds a cylindrical cuvette (about 1 cm in diameter) with two motors that provide a rotational (about 5 rev/sec) and a slower vertical inversion (about 2.5 centimeters per sec) motions. The slow vertical scanning is useful to ensure statistical independence of the observation volumes explored in subsequent vertical sweeps. The illumination focus is centered about 200 μm from the wall of the cuvette inside the sample.

For generating excitation light, an optical source comprising a halogen lamp coupled to a 525 nm band-pass filter with FWHM of 60 nm, an Argon ion laser (Stabilite 2017, Spectra-Physics) providing 515 nm excitation light, or a neodymium-yttrium laser providing 532 nm excitation light is provided. The radiant power of the optical source required for detecting particles in this experimental configuration is less than 1 mW. The objective lens provided is Kyowa 20× (N.A. 0.40). A long pass emission optical filter is provided in front of the photodetector to avoid detection of any excitation light reflected by the dichroic mirror. Fluorescence detection is achieved using a photodetector comprising a photo-multiplier tube (PMT) HC120 (Hamamatsu). The signal from the PMT is fed into a dual-channel 12 bit A/D acquisition card. The photocurrent is sampled with a variable time resolution (1/40 kHz=0.025 ms or less). The time trace of the signal giving the photocurrent per time bin as a function of time is stored in the computer and analyzed using comprehensive analysis software we refer to as simFCS. Among many other functions, simFCS calculates the autocorrelation function and the photon counting histogram. A correlation filter program having a particle passage pattern recognition algorithm is also included in simFCS. The function of the filter is to match a predetermined pattern to features in the temporal profile. The width of the pattern matched to features in the temporal profile correlates with the time of passage of the particle through the illumination volume. The system is configured such that a histogram of positive events is obtained and individual matches are viewable. The correlation filter program based on particle passage pattern recognition allows sub-attomolar detection of particles with low brightness for less than a minute of scanning time.

In the present invention, the total volume that is analyzed during optical analysis is proportional to the total sample scanning period (or detection time). The estimated volume of the Point Spread Function (VPSF) in the confocal microscope is defined by the expression:

$$VPSF = (L_x) \times (L_y) \times (L_z) \tag{I}$$

wherein $L_x$ is the length of the observation along the X direction, $L_y$ is the length of the observation in the Y direction, and $L_z$ is the length of the observation in the Z direction. When a rectangular slit is provided in front of the photodetector, $L_x$ and $L_y$ correspond to axes that are orthogonal to the propagation axis of the excitation light and are calculated using the physical dimensions of the slit and the magnification factor of the confocal microscope, and $L_z$ corresponds to an axis parallel to the propagation axis of the excitation light and is calculated using the physical optics of the system. In an embodiment wherein $L_x$, $L_y$ and $L_z$ are equal to 70 microns, 500 microns and 150 microns, respectively, Equation I provides a volume of the Point Spread Function equal to $5 \times 10^6$ microns$^3$.

$$VPSF = (70 \ \mu m) \times (500 \ \mu m) \times (150 \ \mu m) = 5 \times 10^6 \ (\mu m)^3$$

The total length (L) of the trajectory of the at least partially transparent container holding the sample for a movement scheme involving rotation and vertical inversion is calculated using the expression:

$$L = \pi(d_{cuvette})(v_r)(t) \qquad (II)$$

wherein $d_{cuvette}$ is the diameter of the cuvette. $V_r$ is the rotational velocity of the cuvette and t is the sample scanning period (or detection time). For a sample scanning period equal to 100 sec, a cuvette diameter equal to 1 centimeter and a rotational velocity is equal to 5 revolutions per second, Equation II provides a value of the total length of the trajectory equal to $1.6 \times 10^7$ μm:

$$L = \pi(1 \text{ cm})\left(\frac{5}{\text{second}}\right)(100 \text{ seconds})\left(\frac{1 \times 10^4 \mu m}{1 \text{ cm}}\right)$$
$$= 1.6 \times 10^7 \mu m.$$

The total volume (V) explored during a sample scanning period is provided by the expression:

$$V = (L) \times (\text{Cross Section}) \qquad (III)$$

wherein L is the total length of the trajectory and Cross Section is the cross section of the observation region, such as the cross section of the observation region along an axis parallel to and/or coincident to the propagation axis of the excitation light. In one embodiment wherein $L_y$ and $L_z$ are equal to 500 microns and 150 microns, respectively, the Cross Section is provided by the expression:

Cross Section=$(L_y) \times (L_z)$=(500 μm)×(150 μm)=7.5× $10^4$ μm$^2$.

Substitution of a Cross Section of $7.5 \times 10^4$ microns$^2$ and a total length of the trajectory (L) of $1.6 \times 10^7$ μm (see calculation above) into Equation III results in a total volume (V) explored during scanning equal to 1.2 ml $$V = (1.6 \times 10^7 \mu m) \times (7.5 \times 10^4 \mu m^2) \times \left(\frac{1 cm}{1 \times 10^4 \mu m}\right)^3$$
$$= 1.2 cm^3$$
$$= 1.2 ml.$$

Therefore, more than 1 ml of volume is explored during a 100-sec measurement time in this experimental configuration. This calculation illustrates the ability of the devices and methods of the present invention to detect very low concentrations (a few per milliliter) in reasonably short scanning times.

It is important to note that the sample fluid never "enters" the inner workings of the device. Careful filtering is not necessary to prevent clogging. Frequent cleaning is not needed to prevent contamination or bacterial growth. The sample is also not lost as in flow cytometry. It remains in the cuvette and, thus, can be subjected to other tests if desired. This attribute of the present invention is a significant advantage when working with hard-to-obtain samples.

Figure 3:
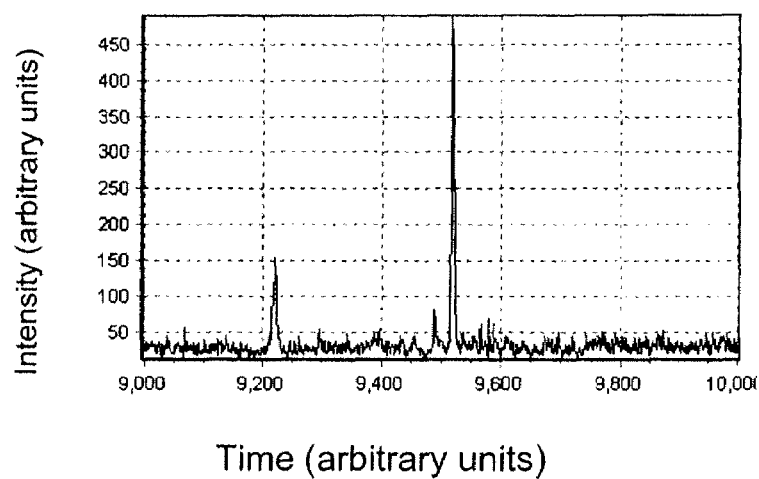
FIG. 3 shows an exemplary fluorescence temporal profile of particles moving through the observation volume generated using the optical analyzer.
Figures 4A, 4B, 4C, 4D:
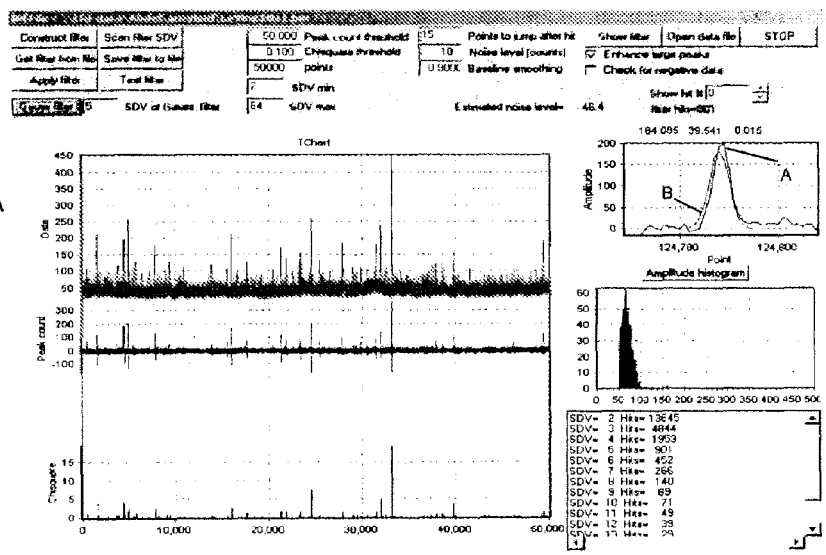
FIG. 4A shows a temporal profile (top plot) generated by the optical analyzer and corresponding predetermined patterns (middle plot) matched to features in the temporal profile. Also shown in FIG. 4A are the chi square values (bottom plot) associated with each pattern matched to the temporal profile.
FIG. 4B provides an overlap plot showing a feature (curve A) observed in a temporal profile and a predetermined pattern (curve B) fit to match to the feature.
FIG. 4C shows the intensity-distribution for a single pattern on an expanded scale and FIG. 4D displays a size distribution obtained for analysis of a heterogeneous sample.

FIG. 3 shows an exemplary fluorescence temporal profile of a particle moving through the observation volume generated using the present optical analyzer. The y-axis corresponds to intensity in arbitrary units and the x-axis corresponds to time in arbitrary units. The temporal profile shown in FIG. 3 was acquired using a combination of rotation of the container holding the sample at a rotational velocity equal to about 300 rotations per minute (5 rev./sec.) and vertical inversion of the container holding the sample at a rate of about 1 centimeter per second. Features in the temporal profile at times equal to about 9,230 and 9,520 correspond to passage of particles through the observation volume. FIG. 4A shows a temporal profile (top plot) generated by the optical analyzer and corresponding predetermined patterns (middle plot) matched to features in the temporal profile. Also shown in FIG. 4A are the chi square values (bottom plot) associated with each pattern matched to the temporal profile. FIG. 4B provides an overlap plot showing a feature (curve A) observed in a temporal profile and a predetermined pattern (curve B) fit to match to the feature. The shape of the predetermined pattern matched to the feature is defined by a Gaussian function. Use of a Gaussian function provides a first approximation for transportation of a particle through the observation volume. Methods of the present invention also include use of predetermined patterns having a more complex functionality, depending on the system and the application. FIG. 4C shows the intensity-distribution for a single pattern on an expanded scale and FIG. 4D displays a size distribution obtained for analysis of a heterogeneous sample.

Figure 5:
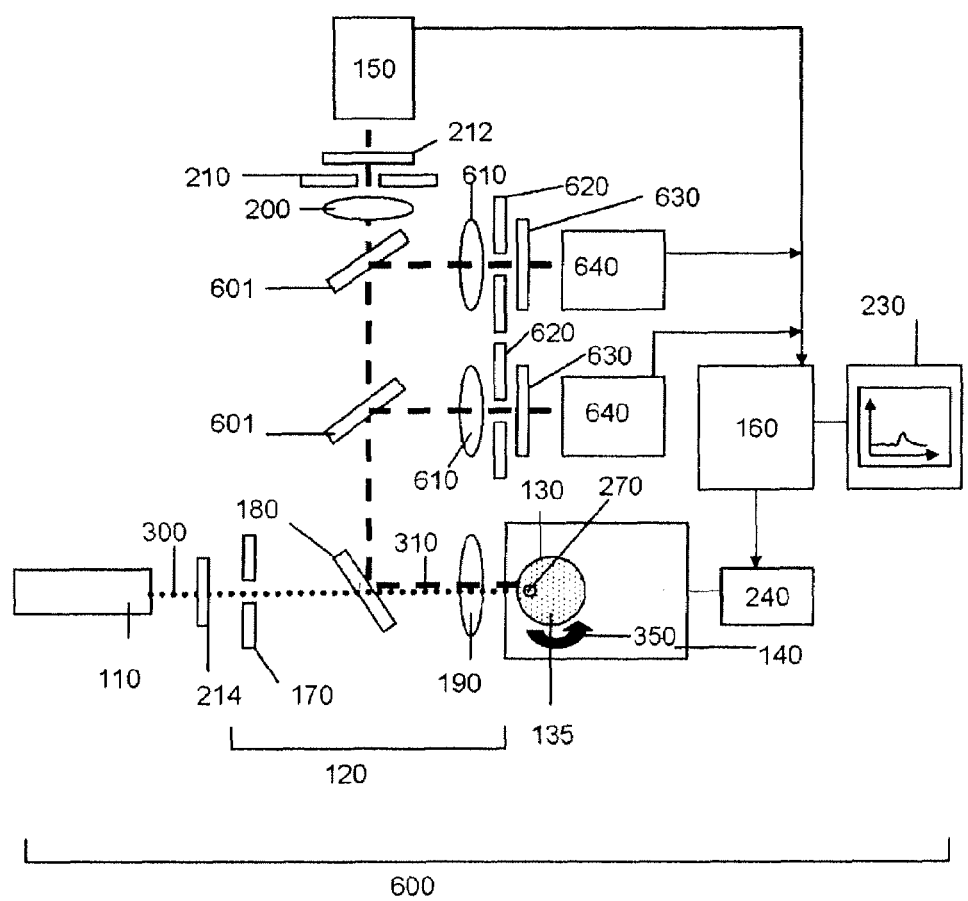
FIG. 5 provides a schematic diagram of a multichannel optical analyzer of the present invention.

FIG. 5 provides a schematic diagram of a multichannel optical analyzer of the present invention. Multichannel analyzer 600 further comprises beam splitters 601, additional objective lens 610, additional confocal apertures 620, additional emission optical filters 630 and additional photodetectors 640. Beam splitters 601 are positioned such that they reflect fluorescence from observation volume 270. As indicated in FIG. 5, this reflected light is passed through additional objective lenses 610 and additional confocal apertures 620, and imaged onto additional photodetectors 640, capable of measuring fluorescence intensities as a function of time. In embodiments of the present invention useful for simultaneously and independently monitoring fluorescence from a plurality of different fluorescent probes associated with particles in the observation region, photodetector 150 and additional photodetectors 640 are each provided with different emission optical filters 630 that transmit light having selected wavelengths distributions. This embodiment of the present invention, therefore, generates a plurality of fluorescence temporal profiles that correspond to signals from different fluorescent probes which can be analyzed to provide information useful for classifying particles on the basis of composition. Alternatively, in other embodiments of the present invention, photodetector 150 and additional photodetectors 640 are each provided with a confocal aperture of a different size. This embodiment of the present invention, therefore, generates a plurality of fluorescence temporal profiles that correspond to observation volumes of different sizes, which can be analyzed to provide information useful for classifying particles on the basis of size and/or shape.

Figure 6:
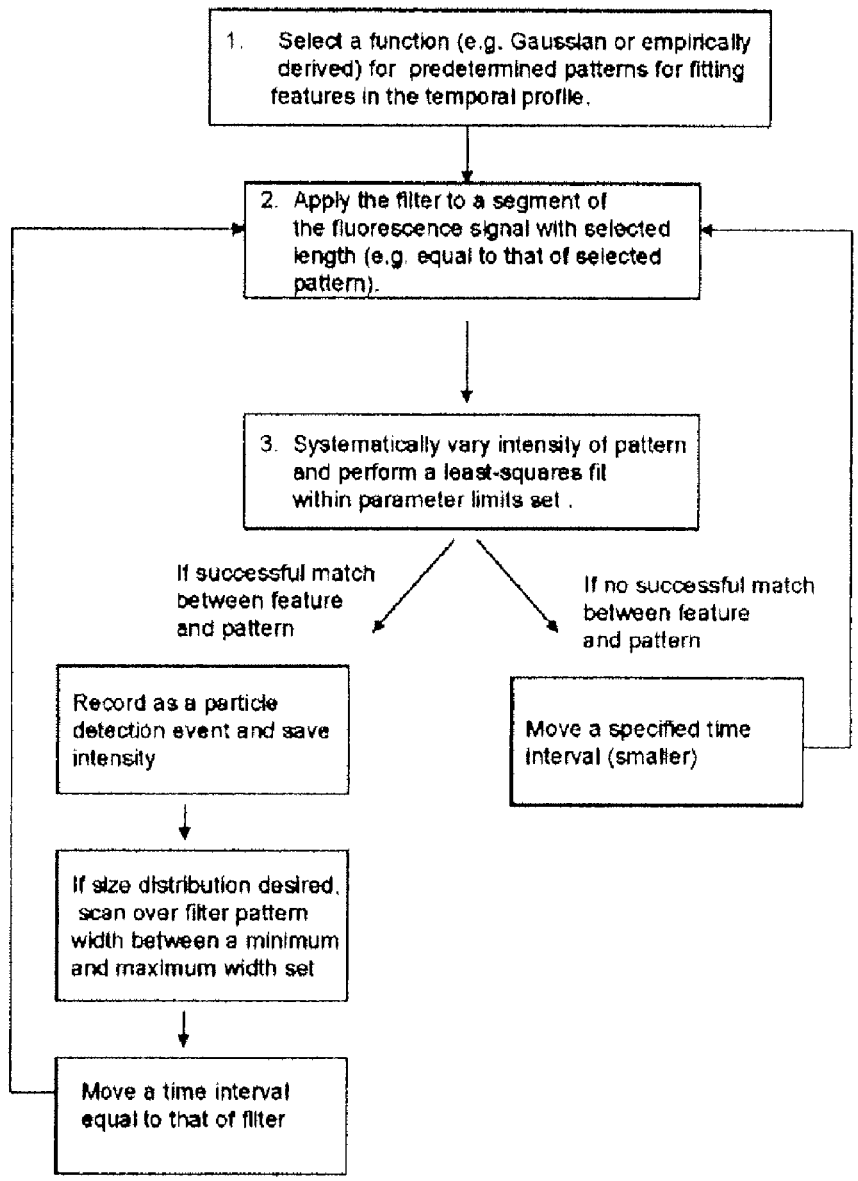
FIG. 6 provides a functional flow diagram illustrating steps in an exemplary pattern recognition algorithm of the present invention.

FIG. 6 provides a functional flow diagram illustrating steps in an exemplary pattern recognition algorithm of the present invention. As shown in this figure, a function type, such as a Gaussian function, is first selected to serve the basis of predetermined patterns that are used to fit features in the temporal profile. Next, the filter is applied to a segment of the fluorescence temporal profile having a selected length, such as a length approximately equal to that of the pattern. The intensity of the predetermined pattern is varied and a least square fit is obtained within a parameter limits set. If a match is obtained, the feature is recorded as a particle detection event and the intensity is saved. If a size distribution is also desired, the pattern width is scanned between a maximum and minimum width set and the width corresponding to the best fit is saved. This process is then repeated for the next time interval of the temporal profile.

The methods and devices of the present invention may use a wide range of optical, electrical and mechanical device components. Optical sources useful in the present methods may comprise narrow band coherent sources, such as lasers, and narrow band lamp sources. Alternatively, broad band lamps may be used as optical sources in the present invention provided that a wavelength filtering element, such as optical interference filter, diffraction grating or monochrometer, is provided to achieve excitation radiation having a sufficiently narrow wavelength distribution to allow sensitive detection of emission from particles in the observation region. Optical sources include, but are not limited to, lasers, narrow band lamps (e.g. mercury arc lamp), broad band lamps (e.g. deuterium lamp, xenon lamp, halogen lamp or fluorescent lamp, one or more light emitting diodes (LEDs).

The present invention is compatible with conventional confocal optical microscopes comprising a collimation element (e.g. pinhole or slit) in optical communication with a light source, dichroic reflector, objective lens and confocal aperture (e.g. pinhole or slit) in optical communication with a photodetector. Use of a collimation element (e.g. pinhole or slit) in optical communication with a light source is optional in the present invention, particularly for embodiment wherein the optical source is a spatially coherent optical source having a small spot size, such as a laser source. Confocal microscopes providing a focal volume having a fixed position are useable in the present invention, as well as confocal microscopes providing a focal volume having a selectively variable position, for example, by rotation of a dichroic reflector. Confocal microscopes in the present invention may have a confocal aperture that has a constant size or a selectively variable size and may be provide in horizontal or vertical optical geometries.

Containers useful in the present methods and devices include containers having any shape that exhibit at least partial transmission of excitation light and emission from particles. Containers useful for optical analysis applications requiring large detection sensitivies are highly transmissive of excitation and emitted light. Use of a container, such as a cylindrical cuvette or optical cell, having a transmittance of excitation light and emission from particles that is substantially constant (e.g. constant to within about 10% or preferably for some applications constant to within about 5%) as a function of rotation position is particularly useful for particle classification measurements wherein the container is rotated during optical analysis.

Any means for moving the container holding the sample container may be used in the present invention that provide translation, rotation or both of the container, including motors, switching electronics and/or eccentric rotating plate mechanisms. Use of means for moving the container holding the sample that are not susceptible to mechanical fluctuations and/or vibrations is preferred for some applications. The optical analysis methods and devices of the present invention, however, are not very susceptible to errors introduced from mechanical fluctuations and/or vibrations that occur on time scales significantly longer (i.e. at least a factor of 3) than the time scale of the passage of particles through the observation volume.

Any photo-detection device is useable in the present invention including, but, not limited to, photomultiplier tubes, photodiodes such as an avalanche photodiode and photoconductive detectors. Photodetectors useful in the present invention may be provided with signal amplifiers, terminators, analog to digital conversion systems, electronic filtering systems or any equivalents known in the art. Photodetectors of the present invention may be configured for photon counting.

The present methods and devices of the present invention are amenable to computer assisted automation and, thus, are well suited to high throughput optical analysis of a large number of samples. Processors useful in the present invention include microcomputers, general-purpose computers or processing systems capable of running application software. Exemplary computers useable in the present methods include microcomputers, such as an IBM personal computer or suitable equivalent thereof, and work station computers. Preferably, pattern recognition algorithms of the present invention are embedded in a computer readable medium, such as a computer compact disc (CD ROM), flash memory device or floppy disc. Further, computer readable medium may be in the form of a hard disk or memory chip, such as random access memory or read only memory.

As appreciated by one skilled in the art, computer software code embodying the data analysis methods and pattern recognition algorithms of the present invention may be written using any suitable programming language. Exemplary languages include, but are not limited to, C or any versions of C, Perl, Java, Pascal, or any equivalents of these. While it is preferred for some applications of the present invention that a computer be used to accomplish all the steps of the present methods, it is contemplated that a computer may be used to perform only a certain step or selected series of steps in the present methods.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. Methods and devices useful for the present methods can include a large number of optional device elements and components including, but not limited to fiber optic elements, temperature controllers, optical filters such as FP etalons, high pass cutoff filters and low pass cutoff filters, collimation elements such as collimating lens and reflectors, trigger pulse generators, lasers, monochrometers, prisms, diffraction gratings, focusing elements such as focusing lens and reflectors, reflectors, polarizers, fiber optic couplers and transmitters, temperature controllers, temperature sensors, broad band optical sources and narrow band optical sources.

The following references relate generally to digital signal processing and pattern recognition (1) *Algorithms and Applications*, John G. Proakis, Dimitris G. Manolakis, Prentice Hall, 3rd edition, 1995; (2) *Discrete Time Signal Processing*, 2nd edition, A. Oppenheim, R. Schafer, and J. Buck, Prentice-Hall, 1999; (3) *Discrete-Time Processing of Speech Signals*, J. R. Deller, Jr., J. H. L. Hansen, and J. G. Proakis, IEEE Press, 1999 and (4) *Pattern Classification* (2001) by Duda, Hart and Stork, Wiley-Interscience. The following references related to analysis methods for interpreting fluorescence data using photon counting histogram analysis and fluctuation correlation spectroscopic analysis: (1) "The Photon Counting Histogram in Fluorescence Fluctuation Spectroscopy", Y. Chen, J. D. Muller, P. T. C. So and E. Gratton, Biophys. J., July 1999, pgs. 553-567, Vol. 77, No. 1; (2) U.S. Pat. No. 6,794,659; (3) "Two photon fluorescence correlation spectroscopy: method and application to the intracellular environment", K. M. Berland, P. T. C. So, and E. Gratton, Biophys. J., 1995, Vol 68, pgs 694-701; (4) "Fluorescence Correlation spectroscopy. I. Conceptual Basis and Theory", E. L. Elson and D. Magde, Biopolymers, 1974, Vol 13, pgs. 1-27; (5) "Fluorescence Correlation spectroscopy. II. An Experimental Realization", D. Magde, E. L. Elson and W. W. Webb, Biopolymers, 1974, Vol 13, pgs. 29-61; (6) "Fluorescence correlation spectroscopy: inception, biophysical experimentations and prospectus", W. W. Webb, Appl. Opt., 2001, Vol 40, pgs. 3969-3983; and (7) Fluorescence-intensity distribution analysis and its application in biomolecular detection technology", P. Kask, K. Palo, D. Ullmann and K. Gall, Proc. Natl. Acad. Sci., 1999, USA, Vol. 96, pgs 13756-13761.

STATEMENTS REGARDING INCORPORATION BY REFERENCE AND VARIATIONS

All references cited throughout this application, for example patent documents including issued or granted patents or equivalents; patent application publications; and non-patent literature documents or other source material are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, materials, reagents, synthetic methods, purification methods, analytical methods, assay methods, and methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

EXAMPLE 1

Analysis of Fluorescent Spheres in Clear and Turbid Media

To verify the ability to accurately measure the concentrations of particles in samples, an optical analysis device of the present invention was used to determine the concentration of orange fluorescent spheres, 1.0 µm in diameter (Molecular Probes, F-8820) in both a clear buffered solution and a Lyposin solution (20% weight diluted 1:80) comprising a scattering sample. A small halogen lamp combined with a green filter (525±60 nm) was used as the optical source to provide excitation light in these measurements. Concentrations of orange fluorescent spheres in these samples as low as a few hundred spheres per milliliter were measurable using the present optical analysis device employing a 1-minute sample scanning time.

Figure 7:
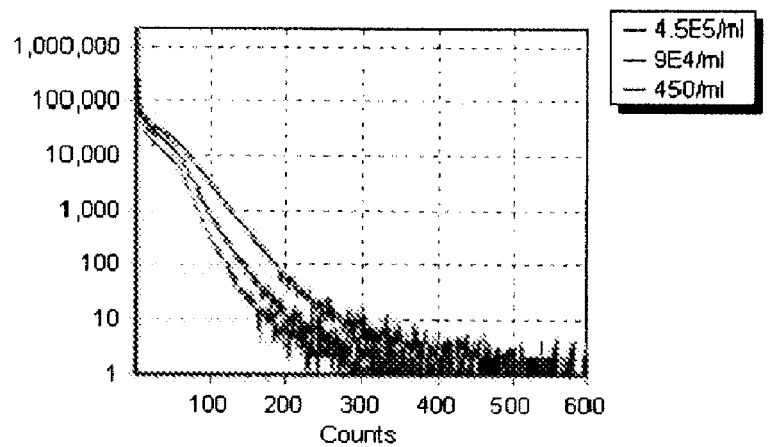
FIG. 7 shows an exemplary photon current histogram generated by the devices and methods of the present invention for a sample containing fluorescent spheres.
Figure 8:
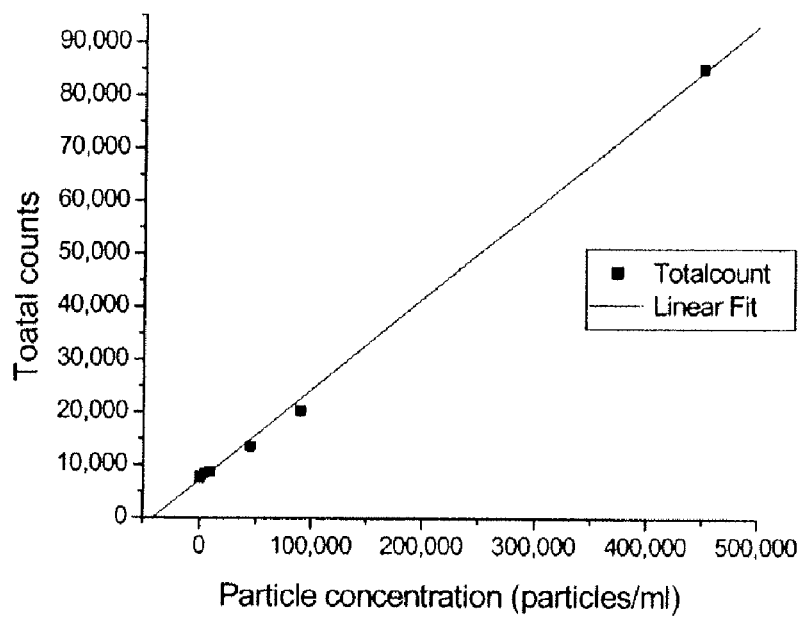
FIG. 8 shows a plot of total counts (peaks in the fluorescence temporal profile) as a function of particle concentrations generated by the devices and methods of the present invention for a sample containing fluorescent spheres.

FIG. 7 shows an exemplary photon current histogram and FIG. 8 shows a plot of total counts (peaks in the fluorescence temporal profile) as a function of particle concentrations generated using the present methods and devices. As shown in FIG. 8, there is a very good linear fit over the wide range of concentrations examined. The results of this study demonstrate that the present methods and devices are well suited for determining the concentrations of fluorescent particles in optically transparent and scattering samples.

In order to reproducibly detect and measure even lower concentrations, for example concentrations as low as a few particles per milliliter, a correlation filter program having a pattern recognition algorithm was used to analyze the fluorescence temporal profiles generated using the present methods. The photon counting histogram includes contributions from the background and effects of the mechanical rotation in addition to the signal from the particles of interest. Simple data filtering (such as low-pass data filtering) is not enough to achieve the targeted detection sensitivity, particularly when dealing with faint particles in a scattering medium. The correlation filter program having a pattern recognition algorithm recognizes the passage of the particle of interest in the illumination volume during the scanning and records the event as a hit, along with its intensity amplitude and optionally its total integrated intensity.

Figure 11:
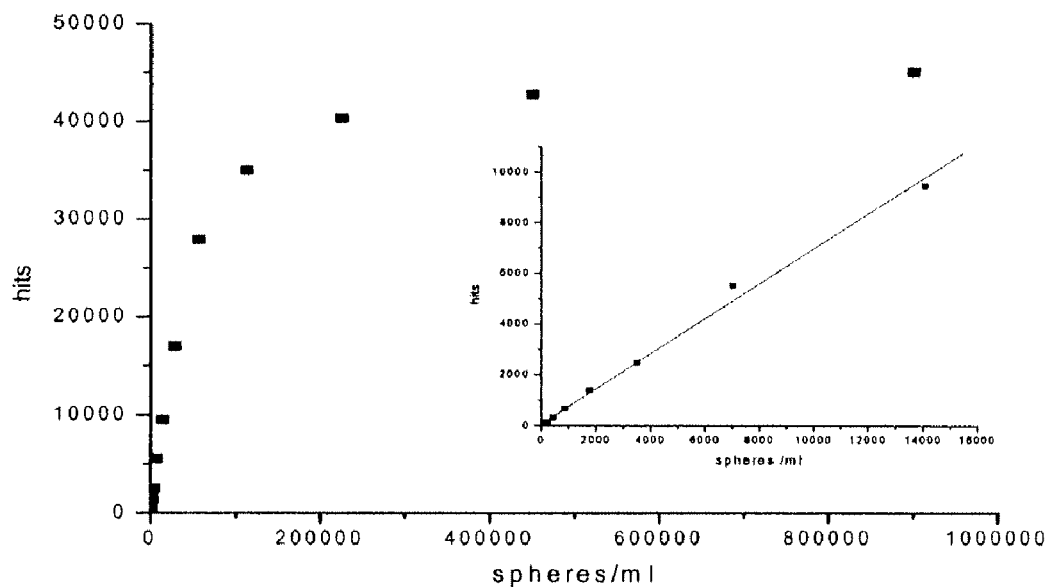
FIG. 11 shows the result of a concentration-dilution study using the present optical analysis device employing pattern recognition data analysis.

To evaluate the effectiveness the pattern recognition algorithm, an instrument calibration was performed using fluorescent fluorospheres. FIG. 11 shows the result of a concentration-dilution study using the present optical analysis device employing pattern recognition data analysis. FIG. 11, shows a saturation of the number of event (particles) detected as the concentration increases. This is an expected result since at high concentration the probability of the simultaneous presence of more than one particle in the volume of observation increases. To correct for the saturation effect, however, is straightforward by decreasing the volume of observation by changing the pinhole in the emission side, performing a linearization of the curve taking into account the pile-up probability, or by simply diluting the sample prior to optical analysis. In the low concentration part of the curve, however, no correction for saturation effects is needed. In this regime, the linearity is excellent down to very low concentrations (few per ml), as shown by the inset in the FIG. 11. For these measurements, a scanning time of about one minute was employed.

EXAMPLE 2

Analysis of the Somatic Cell Count in Milk

Mastitis is the most costly disease of dairy cattle. Estimates of the total losses due to this disease in the U.S. are in the range of 1.5 to 3.0 billion dollars annually. Since cell counts in milk are closely associated with udder health, the somatic cell count (SCC) is accepted as an international standard measurement of milk quality. As a result, inexpensive, reliable and portable methods and devices for measuring the somatic cell count in milk are currently needed.

The ability of optical analysis devices of the present invention to determine the concentration of somatic cells in milk was experimentally verified. In these measurement, fresh milk was obtained from the dairy cattle research unit of the University of Illinois. Milk samples were diluted to ¼ in TRIS buffer prior to analysis. Initially experiments were performed on a sample comprising milk from a cow undergoing treatment for Mastitis. The somatic cell count corresponding to milk from this source was determined to be approximately 1,000,000 cells per milliliter. In these experiments, ten dilutions were performed to allow analysis of diluted sample having somatic cell counts ranging from about $10^5$ cells per mL to about $10^6$ cells per mL. A detergent (Triton-X 100) was added to the samples prior to optical analysis to rupture the cell membranes. In addition, ethidium bromide (Molecular Probes, E-1305) was added at a concentration of 10 micromolar to fluorescently label the somatic cells. The added ethidium bromide associates with DNA in the cells, wherein its fluorescence is enhanced by a factor of about twenty over that of the free form.

Figure 9:
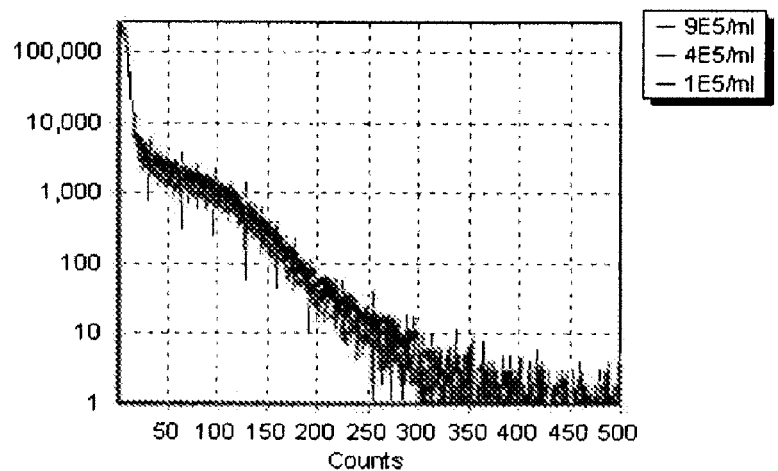
FIG. 9 shows an exemplary photon current histogram generated by the present methods for a milk sample containing somatic cells.
Figure 10:
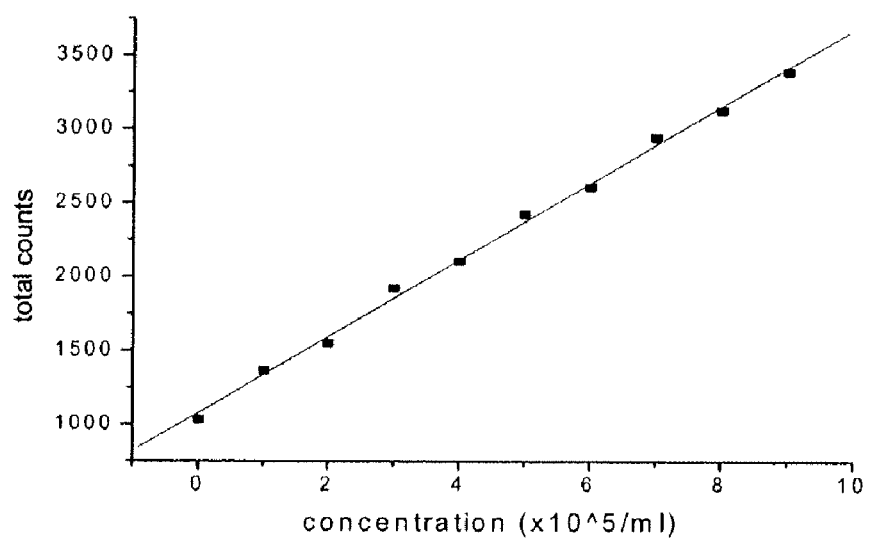
FIG. 10 shows a plot of total counts (peaks in the fluorescence temporal profile about the threshold) as a function of somatic cell concentrations generated using the present methods and devices.

FIG. 9 shows an exemplary photon current histogram generated by the present methods for a milk sample containing somatic cells. The broadening of the histogram in FIG. 9 clearly depends on the concentration of fluorescent particles in the sample. To generate a useful calibration curve for this system, a fluorescence intensity threshold was set establishing which features in the fluorescence temporal profile are identified as a positive detection of a somatic cell. FIG. 10 shows a plot of total counts (peaks in the fluorescence temporal profile about the threshold) as a function of somatic cell concentrations generated using the present methods and devices. As shown in FIG. 10, there is a very good linear fit over the useful range of concentrations examined. Furthermore, repeated analysis of the raw data indicated that the linearity of the calibration curve is not very sensitive to the choice of the fluorescence intensity threshold.

EXAMPLE 3

Optical Analysis of *E. Coli* Bacteria

Figure 12:
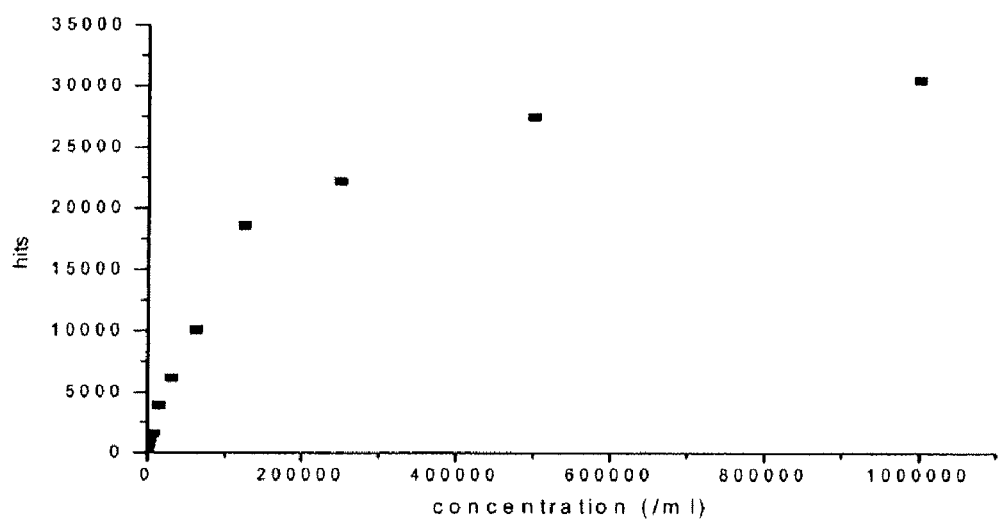
FIG. 12 shows the calibration generated from fluorescence temporal profiles corresponding to the significantly dimmer fluorescence of the bacteria.
Figure 13:
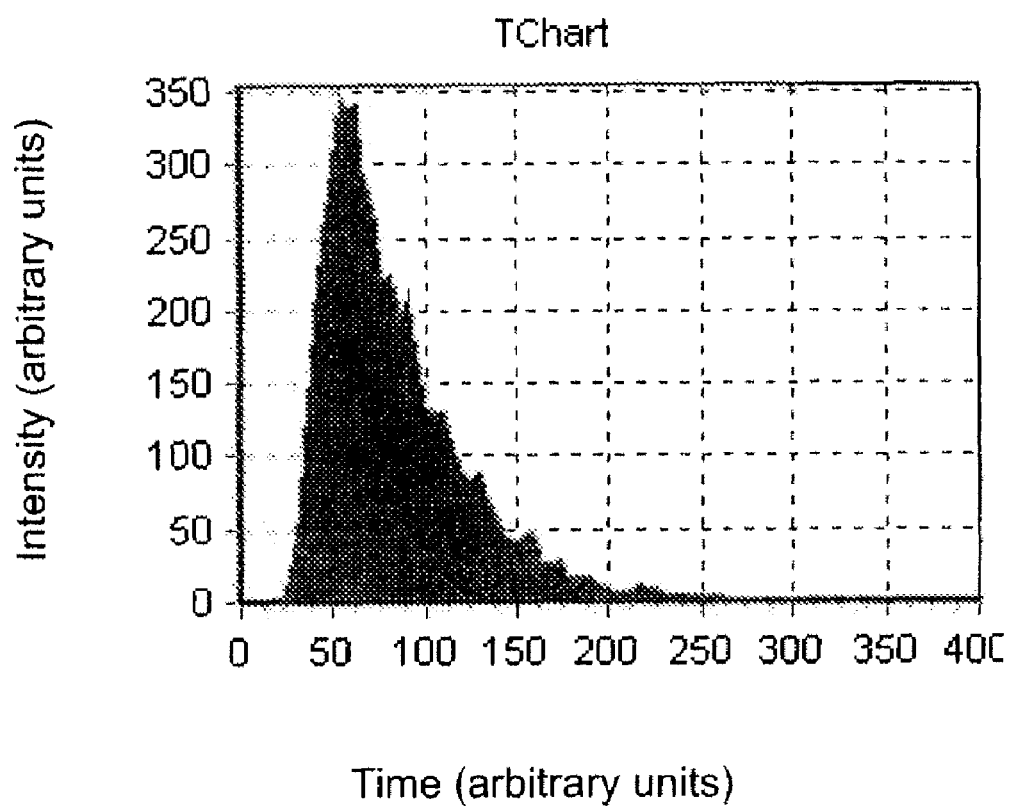
FIG. 13 provides an amplitude histogram (i.e. intensity distribution), which demonstrates the ability of the present methods to classify particles based on their intensity distribution.

The ability of the present invention to measure the concentration of microoganisms, such as bacteria, was verified experimentally. In these experiments, *E. coli* bacteria were left to multiply for several hours in Luria Broth at a temperature of 37° C. and 300 rotations-per-minute agitation in an incubator shaker (New Brunswick Scientific, C24). A MOPS buffer solution was then used for sample dilutions. The bacteria were tagged with Sytox Orange, a DNA probe. FIG. 12 shows the calibration generated from fluorescence temporal profiles corresponding to the significantly dimmer fluorescence of the bacteria. As shown in FIG. 12, concentrations well below 100 per milliliter are able to be measured employing a 1-minute scanning time. In addition, the software used for data analysis also performed an intensity analysis. FIG. 13 provides an amplitude histogram (i.e. intensity distribution), which demonstrates the ability of the present methods to classify particles based on their intensity distribution.

EXAMPLE 4

Optical Detection of Aβ Protein Aggregates

A goal of the present invention is to detect and measure the concentrations of aggregates of proteins in biological samples, such as bodily fluids. To evaluate this application of the present invention, the ability of the present optical analysis devices and methods to measure low concentrations of aggregates of Amyloid P oligomers was verified experimentally.

Cerebrospinal fluid samples from Alzheimer's disease and age-matched control subjects obtained at autopsy (n=19 AD; n=21 C average postmortem interval <3.5 hrs) were labeled with fluorescein-human Aβ(1-42) (FL42) (Anaspec, Inc.) and assayed by FCS according to methods modified from Pitschke. Two photon excitation (780 nm, Ti:Sapphire laser, mode-locked, 150 fs pulses, 6-9 mW at the sample) was employed to reduce photodamage to the probe and better define the sampling volume. Detection was with an EG&G model SPCM-AQR-15 avalanche photodiode operated in the photon-counting mode. The laser illumination was focused on a 10 µl sample droplet in an 8-chamber slide (LabTech cat. 15541) through a 40X NA=1.4 oil objective. Single molecule detection and correlation analysis of fluorescein and fluorescein-lysozyme were used to calibrate the instruments. 16-bit data sampling rates ranged from 16-32 kHz to discern single molecule events.

FL-42 in 10 mM NaPi-0.2% w/v SDS, pH 7.5 was diluted to 100 nM and 0.02% SDS in the CSF sample to label the endogenous oligomeric complexes. Large bright particles were observed in the AD samples above the free fluorescent peptide background. Neither the unlabeled CSF samples nor 100 nM FL-42 in 10 mM NaPi, pH 7.5 generated the large bright oligomers observed in the labeled CSF samples over the time of the measurements.

The large bright oligomers were detected as rare events, estimated number concentration <1 pM. These large oligomers diffused slowly and most of the sampling time was waiting between events. We would anticipate that the combination of low concentration and slow diffusion of oligomers would require days for a single determination with sufficient statistics.

In order to collect enough events to make meaningful comparisons in minimal time, several beam-scanning paradigms were tested to increase the volume sampled while retaining the resolution to distinguish individual molecules. Without scanning the confocal image continuously monitored a volume of ~1 fl. Scanning the focal point in a 20 μm diameter circle with a 4 msec period sampled a volume of ~0.5 μl. Raster scanning 45×45 μm in X-Y and 60 μm Z-axis in 3 μm increments sampled ~120 pl.

Figure 14A:
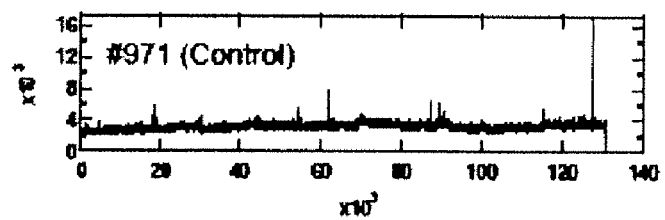
FIGS. 14A and 14B show fluorescence temporal profiles for control and AD samples, respectively.
Figure 14B:
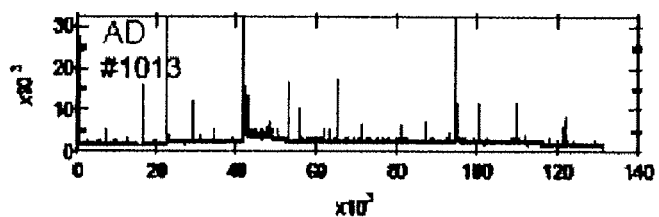
Figure 14C:
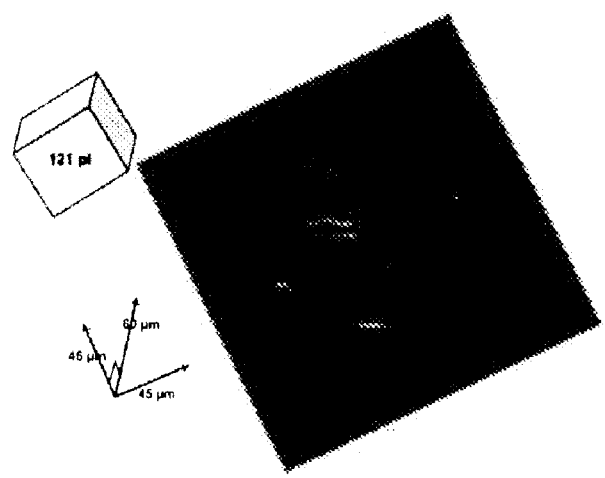
FIG. 14C shows a quasi 3-D image generated from a 3-D scan, and indicates number of large fluorescent oligomers (elongated white spots).

FIGS. 14A and 14B show fluorescence temporal profiles for control and AD samples, respectively, obtained using a conventional scanning confocal microscope operating in two photon excitation mode. FIG. 14A corresponds to static-control & AD (20 min) and FIG. 14B correspondence to 3-D AD sample beam scan (XY raster scan+z-step; 90 sec. The intense spikes in FIG. 14A were interpreted as large oligomeric Aβ complexes based on their slow diffusion, as indicate by the measured peak widths. In this small sample of autopsy CSF samples, the control group (n=22, average 3.105±0.648 peaks S.D.) can be distinguished from the AD group of subjects (n=18, average 6.053±0.800 peaks S.D.) at p=0.00346. Although the groups are separable, the populations overlap, due in part to the small number of events observed. The 3-D scan shown in FIG. 14B was converted into a quasi-3-D image. FIG. 14C shows a quasi 3-D image generated from a 3-D scan, and indicates number of large fluorescent oligomers (elongated white spots).

Figure 15:
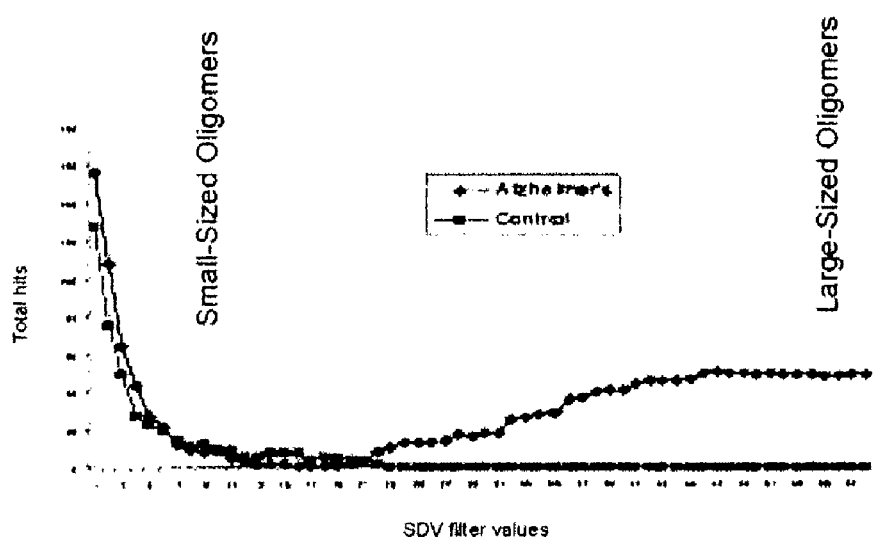
FIG. 15 provides a correlation plot of aggregate concentration and size for the control samples and the AD samples.

The correlation filter program having a pattern recognition algorithm was used to analyze the fluorescence temporal profiles acquired using the present methods and devices and to determine the distribution of sizes for the elongated particles, such as the Amyloid β polymers and aggregates. FIG. 15 provides a correlation plot of aggregate concentration and size for the control samples and the AD samples.

EXAMPLE 5

Optical Analyzer Having a Multi-Slit Confocal Aperture for Better Localization and Intrinsic Brightness Determination Optionally, optical analyzers and analysis methods of the present invention utilize a multi-slit confocal aperture optical configuration. Analyzers of this aspect of the present invention are capable of measuring the position and/or trajectory of particles in the observation volume, in addition to providing measurements of particle concentration, particle brightness and/or size characterization. This functional aspect of the present invention allows for accurate optical analysis using large observations volumes, thereby enabling analysis of large sample volumes during optical scanning. Determination of particle position and/or trajectory in these embodiments provides enhanced sensitivity for detecting particles and characterizing particles with respect brightness because the position information acquired during analysis removes and/or minimizes uncertainties relating to the absolute intensities or brightness of particles detected.

In this embodiment of the present invention, a multi-slit confocal aperture is provided between the sample and the photodetector such that at least a portion of the fluorescence from the observation volume passes through the multi-slit confocal aperture prior to detection by the photodetector. As used herein the term "multi-slit confocal aperture" refers to a device component comprising a plurality of slits and/or pinholes, which are symmetrically or asymmetrically spatially distributed in front of the photodetector and which allow at least partial transmission of incident fluorescence. Multi-slit confocal apertures may have any number of slits and/or pinholes providing accurate optical detection and/or characterization of particles, and the slits or pinholes provided may have the same or different areas. Use of a dual-slit confocal aperture (i.e. having two slits) comprising two confocal slits having substantially the same slit areas (e.g. within about 10%) is beneficial for some optical analysis applications. In embodiments of this aspect the present invention, the multi-slit confocal aperture may be a component of a confocal microscope. Useful multi-slit confocal apertures for some applications of the present invention comprise a plurality of slits having widths selected over the range of about 5 micron to about 100 microns that are equally spaced apart from each other by distances selected over the range of about 5 microns to about 500 microns. Useful multi-slit confocal apertures for some applications of the present invention comprise a plurality of slits that are symmetrically distributed in front of a photodetector.

Figure 16A:
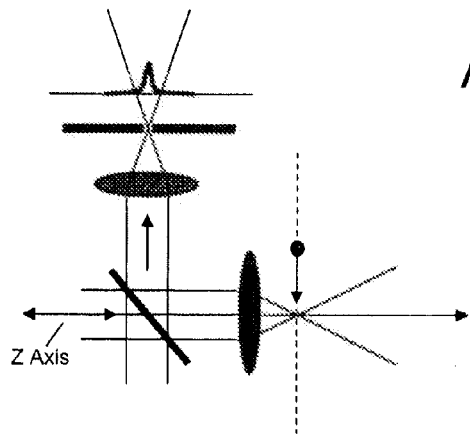
FIGS. 16A-16D schematically illustrate use of a multi-slit confocal aperture in the present invention for determining particle positions in the observation volume.
Figure 16B:
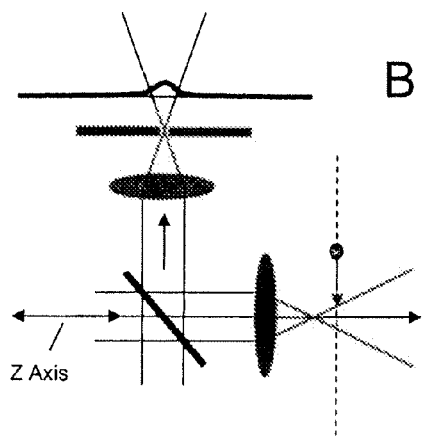
Figure 16C:
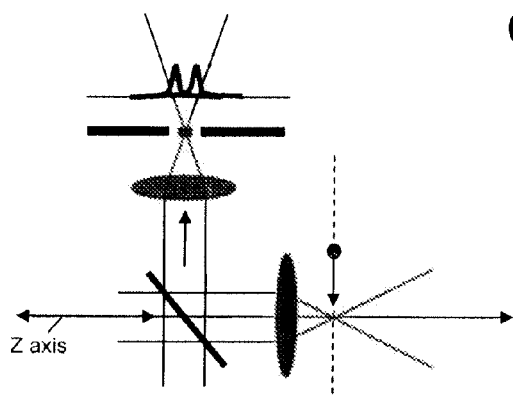
Figure 16D:
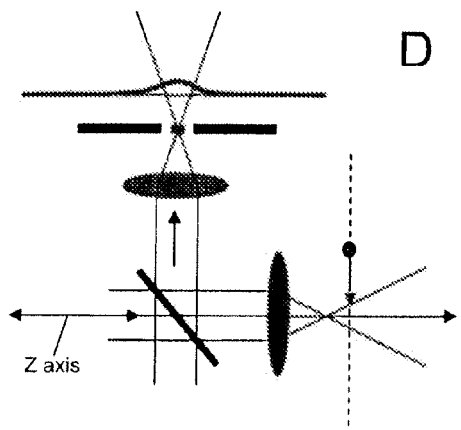

In the present analyzers and analysis methods a multi-slit confocal aperture is used to enhance the determination of positions and/or trajectories of fluorescent particles with respect to the center of the illumination profile. The present multi-slit configuration employs multiple slits in front of a single. photodetector, as opposed to a single slit positioned in front of a single detector. FIGS. 16A-16D schematically illustrates and compares use of single-slit and multi-slit confocal apertures in the present invention for determining particle positions and/or trajectories in the observation volume. FIGS. 16A and 16B depict embodiments of the present invention using a single-slit confocal aperture and FIGS. 16C and 16D depict embodiments of the present invention using a dual-slit confocal aperture.

FIGS. 16A and 16B show a first particle trajectory (16A) passing exactly in the center of the confocal volume and a second particle trajectory (16B) passing away from the center of the confocal volume. FIGS. 16A and 16B (top of these panels) also indicate the fluorescence temporal profiles predicted for each single slit confocal aperture configuration. A comparison of FIGS. 16A and 16B shows that as the particle passes away from the center of the observation volume, the width of the fluorescence temporal profile increases. Therefore, measurement of the widths of features of the temporal profile provides a means of determining particle position and/or trajectory.

Incorporation of a multi-slit confocal aperture substantially increases the precision and accuracy of measured particle positions and/or trajectories. FIGS. 16C and 16D show a first particle trajectory (16C) passing exactly in the center of the observation volume and a second particle trajectory (16D) passing away from the center of the observation volume. FIGS. 16C and 16D (top of these panels) also indicate the fluorescence temporal profiles predicted for each dual-slit confocal aperture configuration. FIG. 16C shows that when the particle passes exactly through the center of the observation volume (i.e. the confocal volume) the temporal profile is characterized by two identical sharp peaks. As indicated in FIG. 16D, however, the two peaks broaden and eventually merge in a single broad peak (16D) in the fluorescence temporal profile as the particle trajectory moves away from the center of the observation volume. This transition from two peaks to a single peak in the fluorescence temporal profile provides a useful means of characterizing particle position and/or trajectory. In one embodiment, for example, the separation in time between peaks in an observed temporal profile corresponding to a given detection event is used to quantitatively characterize the position of the particle in the observation volume (for example, the position of the particle along the Z-axis as shown in FIG. 16A-16D). The time separating two maxima in a temporal profile acquired using a multi-slit confocal aperture optical geometry provides important information useful for measuring particle position, particle trajectory and/or brightness intensity with enhanced accuracy. Changes in peak shape and spacing observed using a multi-slit confocal aperture optical geometry may also be used in the present invention to determine particle shape.

When a particle passes through the observation volume, the measured fluorescence depends on the intrinsic brightness (or intensity) of the particle and the specific position of its trajectory in the illumination profile, the brightness being higher closer to the center of the confocal volume. In one embodiment, the system is capable of analyzing different fluorescence temporal profiles generated using the multi-slit configuration (for example by measuring the separation in time of two or more peaks in an observed temporal profile) and properly assigning the position of the particle along the Z-Axis (as identified in FIGS. 16A-16D). Once the particle position along the Z-Axis (as identified in FIGS. 16A-16D) is known, the particle intensity/brightness can be calculated with enhanced accuracy. Using this new approach, there is still indetermination, reflection symmetry with respect to the focal plane, which does not affect the calculation of the illumination intensity. Analysis of temporal profiles generated using a multi-slit confocal aperture optical geometry may be analyzed using a variety of methods including, but not limited to pattern recognition data analysis techniques, photon counting histogram analysis and fluctuation correlation spectroscopy methods.

We claim:

1. A device for analyzing particles in a sample; said device comprising:
   an at least partially transparent container for holding said sample containing said particles;
   an optical source for generating excitation light that is provided to said sample, thereby causing at least a portion of said particles to generate fluorescence;
   a means for collecting fluorescence from an observation volume positioned within said container;
   a means for moving said container, thereby transporting at least a portion of said particles through said observation volume;
   a photodetector in optical communication with said means for collecting fluorescence for receiving and measuring intensities of at least a portion of said fluorescence from said observation volume; thereby generating a temporal profile of said fluorescence; and
   a processor having a pattern recognition algorithm for receiving and analyzing said temporal profile generated by said photodetector,
   wherein said observation volume is positioned a distance from a wall of said container selected from the range of about 100 microns to about 2000 microns.

2. A device for analyzing particles in a sample; said device comprising:
   an at least partially transparent container for holding said sample containing said particles;
   an optical source for generating excitation light that is provided to said sample, thereby causing at least a portion of said particles to generate fluorescence;
   a means for collecting fluorescence from an observation volume positioned within said container;
   a means for moving said container, thereby transporting at least a portion of said particles through said observation volume;
   a photodetector in optical communication with said means for collecting fluorescence for receiving and measuring intensities of at least a portion of said fluorescence from said observation volume; thereby generating a temporal profile of said fluorescence; and
   a processor having a pattern recognition algorithm for receiving and analyzing said temporal profile generated by said photodetector, wherein a predetermined pattern is matched to a feature of said temporal profile when the width of the predetermined pattern correlates with the time of flight of a particle passing through said observation volume.

3. A method for analyzing particles in a sample containing said particles, said method comprising the steps of:
   providing said sample containing particles in an at least partially transparent container;
   directing excitation light onto said sample, thereby causing at least a portion of said particles in said sample to generate fluorescence
   collecting fluorescence from an observation volume in said sample and directing said fluorescence from said observation volume onto a photodetector;
   moving said container thereby passing particles in said sample through said observation volume;
   measuring the intensity of said fluorescence from said observation volume as a function of time using said photodetector, thereby generating a temporal profile of said fluorescence from said observation volume; and
   analyzing said temporal profile using a pattern recognition algorithm, wherein said step of analyzing said temporal profile using said pattern recognition algorithm comprises the steps of matching features in said temporal profile to predetermined patterns, counting the number of matches between features in said temporal profile and said predetermined patterns, thereby determining a net number of particles detected during a detection time interval, and dividing the net number of particles detected during said detection time interval by a total volume of sample scanned during said detection time interval.

4. The method of claim 3 wherein said container is cylindrical, wherein said step of moving said container comprises simultaneously rotating and vertically inverting said containing, and wherein said step of analyzing said temporal profile using said pattern recognition algorithm further comprises the step of determining a total length of a trajectory of said observation volume in said sample using the expression:

$$L = \pi(d)(V_r)(t);$$

wherein d is the diameter of the container, $V_r$ is the rotational velocity of the container and t is the selected detection time interval.

5. The method of claim 4 wherein said total volume (V) of sample scanned during said detection time interval is provided using the expression:

$$V = (L) \times (\text{Cross Section});$$

wherein L is the length of said selected trajectory and Cross Section is a cross sectional area of the observation volume along an axis parallel to the propagation axis of said excitation light.

* * * * *